(12) United States Patent
Wang et al.

(10) Patent No.: US 8,071,609 B2
(45) Date of Patent: Dec. 6, 2011

(54) UNSATURATED HETEROCYCLIC DERIVATIVES

(75) Inventors: Yihan Wang, Newton, MA (US); Wei-Sheng Huang, Acton, MA (US); Rajeswari Sundaramoorthi, Chennai (IN); Xiaotian Zhu, Newton, MA (US); R. Mathew Thomas, Sharon, MA (US); William C. Shakespeare, Southborough, MA (US); David C. Dalgarno, Brookline, MA (US); Tomi K. Sawyer, Southborough, MA (US)

(73) Assignee: ARIAD Pharmaceuticals, Inc., Cambridge, MA (US)

( * ) Notice: Subject to any disclaimer, the term of this patent is extended or adjusted under 35 U.S.C. 154(b) by 550 days.

(21) Appl. No.: 11/990,299

(22) PCT Filed: Aug. 11, 2006

(86) PCT No.: PCT/US2006/031382
§ 371 (c)(1), (2), (4) Date: Oct. 16, 2008

(87) PCT Pub. No.: WO2007/021937
PCT Pub. Date: Feb. 22, 2007

(65) Prior Publication Data
US 2009/0156596 A1 Jun. 18, 2009

Related U.S. Application Data

(60) Provisional application No. 60/707,423, filed on Aug. 11, 2005.

(51) Int. Cl.
| C07D 473/16 | (2006.01) |
| C07D 473/34 | (2006.01) |
| A61K 31/52 | (2006.01) |
| C07F 9/6561 | (2006.01) |
| C07D 473/40 | (2006.01) |
| A61P 35/00 | (2006.01) |

(52) U.S. Cl. .................. 514/263.2; 514/81; 514/234.2; 514/263.1; 514/263.21; 514/263.24; 514/263.37; 514/263.4; 544/81; 544/244; 544/276; 544/277; 548/239; 548/331.1; 548/362.5

(58) Field of Classification Search .................. 514/81, 514/234.2, 263.1, 263.2, 263.21, 263.22, 514/263.24, 263.3, 263.37, 263.4; 544/118, 544/244, 276, 277
See application file for complete search history.

(56) References Cited

U.S. PATENT DOCUMENTS
2005/0054614 A1   3/2005  Daicovo et al.

FOREIGN PATENT DOCUMENTS
| WO | WO 98/05335 | 2/1998 |
| WO | WO 00/49018 | 8/2000 |

OTHER PUBLICATIONS
Zhou, Chem Biol Drug Des 2010; 75: 18-28.*
Huang et al, "Facile Synthesis of . . . and aryl halides", Tetrahedron Letters, Aug. 6, 2007, p. 7388-7391, vol. 48, No. 41.
Joshi et al, "Ynamines Derived from . . . and Biological Activity", J. of the Chem. Soc., Chem Commun., Mar. 1, 1992, pp. 513-514, vol. 1992.
EP Search Report, Appl. No. 06813381.8, Aug. 16, 2010.

* cited by examiner

*Primary Examiner* — Mark Berch
(74) *Attorney, Agent, or Firm* — David L. Bernstein

(57) ABSTRACT

This invention relates to compounds of the general formula:

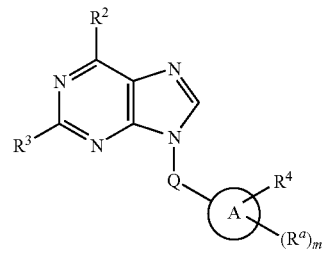

in which Q is an ethynyl or ethenyl moiety; Ring A is an aryl, heteroaryl or heterocyclic ring or ring system; and the remaining variable groups are as defined herein, and to their preparation and use.

17 Claims, No Drawings

UNSATURATED HETEROCYCLIC DERIVATIVES

RELATED APPLICATIONS

The present application claims benefit under 35 U.S.C. §371 of International Application No. PCT/US2006/031382 (published PCT application No. WO 2007/021937), filed Aug. 11, 2006, which claims priority to 35 U.S.C. §119(e) to U.S. Provisional Patent Application No. 60/707,423, filed Aug. 11, 2005, the entire contents of which are hereby incorporated by reference.

BACKGROUND OF THE INVENTION

The purine ring system has been explored in some detail by academic and industrial researchers, leading to the production and evaluation of a variety of derivatives for various applications. This invention concerns a new family of purine derivatives and their use in treating cancers, bone disorders, metabolic disorders, inflammatory disorders and other diseases.

DESCRIPTION OF THE INVENTION

1. General Description of Compounds of the Invention

The compounds of this invention have a broad range of useful biological and pharmacological activities, permitting their use in pharmaceutical compositions and treatment methods for treating metabolic disorders, bone diseases (e.g., osteoporosis, Paget's Disease, etc.), inflammation (including rheumatoid arthritis, among other inflammatory disorders) or cancer (including solid tumors and leukemias, especially those mediated by one or more kinases such as Src or kdr, or by dysregulation of a kinase such as Abl), including, among others, cases which are resistant or refractory to one or more other treatments. Included are compounds of Formula I:

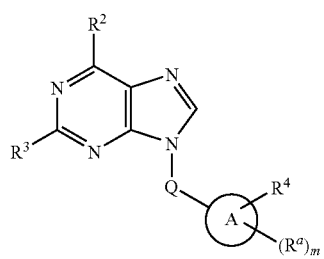

(I)

in which:
each occurrence of $R^2$ is halogen, R, —OR, —SR, —NR$^6$R$^7$, —CONR$^6$R$^7$ or —NRCO(VR), where V is —O—, —S—, —NR—, or a covalent bond;
each occurrence of $R^3$ is -M$_k$R$^C$, where each M is independently a substituted or unsubstituted methylene moiety; k is an integer from 0 through 4; R$^C$ is a halogen, —CN, R, —OR, —S(O)$_n$R, —S(O)$_n$NRR', —NRR', —NR(CO)VR, —CO(VR) or J, a phosphorus-containing moiety defined below; and, n is 0, 1 or 2;
each occurrence of $R^4$ is R, —CONR$^6$R$^7$, —NHCOR$^6$, —NHCO(OR$^6$) or —NHCONR$^6$R$^7$;

each occurrence of $R^6$ and $R^7$ is independently H or is an aliphatic, heteroaliphatic, aryl or heteroaryl group, or NR$^6$R$^7$ constitutes a N-containing heterocyclic or heteroaryl ring or ring system;
Q is —CC— or —CR=CR'— (in either cis- or trans- orientation);
Ring A is an aryl, heteroaryl or heterocyclic ring or ring system;
$(R^a)_m$ represents one or more optional substituents ($R^{a1}$, $R^{a2}$, $R^{a3}$, etc) (permitted for an aryl, heteroaryl or heterocyclic ring system, as defined below, wherein m is an integer from zero up to the number of substituents permitted on the given ring system, in many cases an integer from 0 through 4; and
each occurrence of R (or R", R''', etc.) without a further alphanumeric superscript is independently hydrogen or an aliphatic, heteroaliphatic, aryl or heteroaryl moiety; and
J is a P-containing moiety of the formula —PO(VR)$_2$, —P(VR)$_2$ or —PO(VR)(GR$^1$) wherein G is O, S, NR or (M)$_x$, and each occurrence of M is independently a substituted or unsubstituted methylene moiety; x is an integer from 1 through 6; and R$^1$ is —PO(VR)$_2$, —SO$_2$(VR) or —C(O)(VR); so long as any R group linked directly to P is not H (e.g., —PR cannot be —PH);

wherein in each of the foregoing groups, each aliphatic or heteroaliphatic moiety may be branched or unbranched, cyclic or acyclic, substituted or unsubstituted, and may contain one or more unsaturated bonds; each aryl and heteroaryl moiety may be substituted or unsubstituted and a heterocyclic or heteroaryl moiety may be covalently linked to an adjacent moiety via one (or, in some cases, more than one) carbon or heteroatoms of the heterocyclic or heteroaryl ring.

The foregoing definitions are further elaborated upon and exemplified below and apply to all subsequent occurrences except to the extent otherwise specified.

2. Featured Classes of Compounds and their Use, Generally

One class of compounds which is of special interest for use in this invention contains compounds of Formula I, as are described just above in Part 1, in which $R^4$ is H and include compounds of vinyl and acetylenic compounds of the following formulas, in which the variable groups are as defined above:

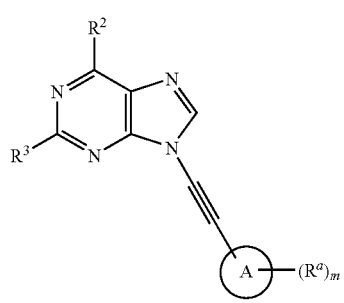

II(a)

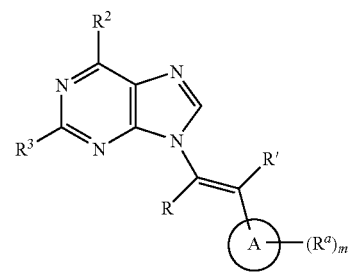

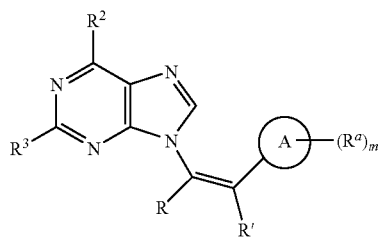

This class is illustrated by compounds of any of the preceding formulas in which Ring A is of one of the following types:

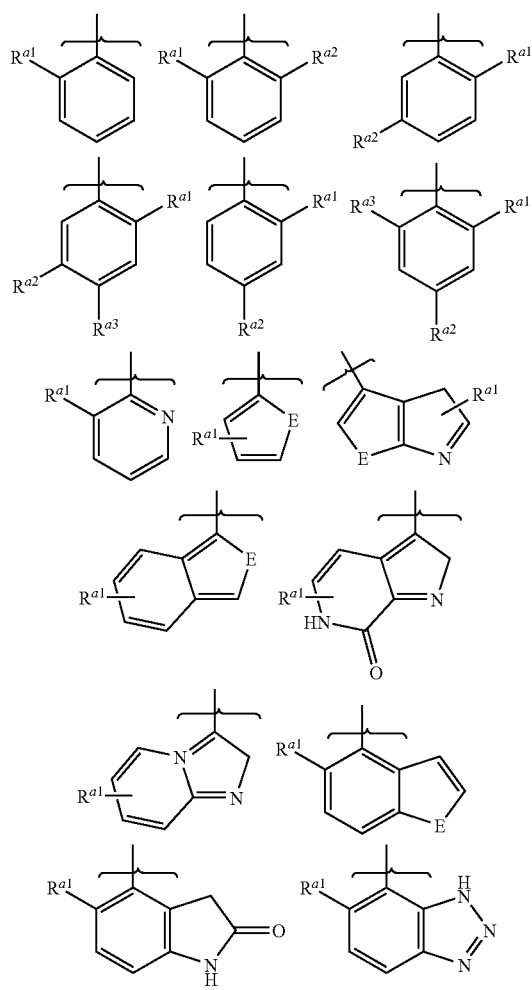

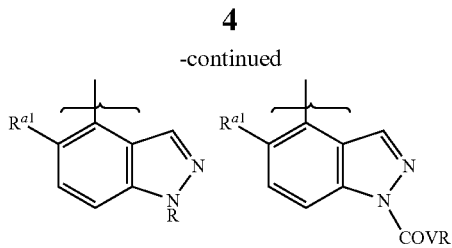

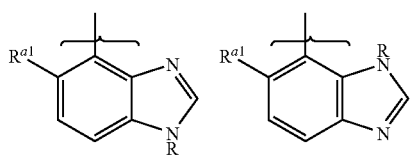

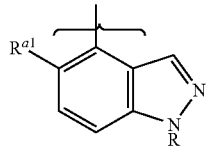

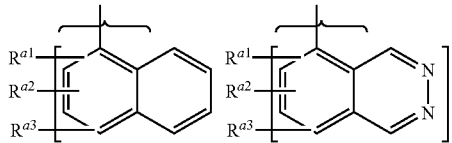

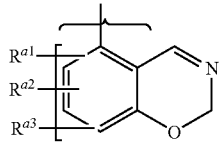

in which $R^{a1}$, $R^{a2}$ and $R^{a3}$ are each independently selected from substituents permitted on an aryl, heteroaryl or heterocyclic group, such as, H, halo, cyano, lower alkyl (methyl, ethyl, n-propyl, i-propyl, cyclopropyl, etc.), haloalkyl, trihaloalkyl (e.g., trichloromethyl, trifluoromethyl, etc.), alkoxy ($CH_3O—$, $CH_3CH_2O—$, $CH_3O\ CH_2O—$, etc.), —S(O)$_n$R, —S(O)$_n$NRR', —NRR', —NR(CO)VR, —CO(VR) or J; and E is O, S or NR.

Illustrative examples of such compounds include those in which Ring A is:

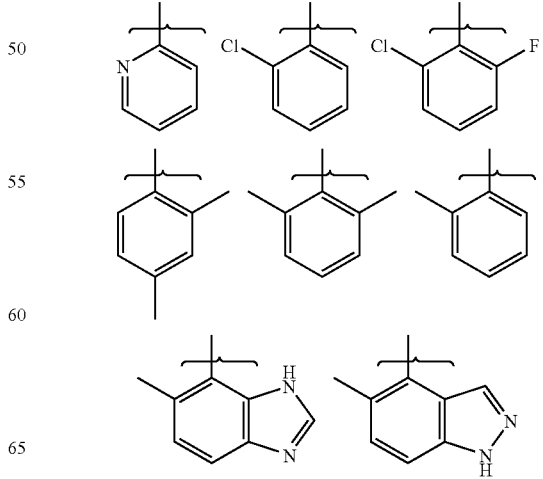

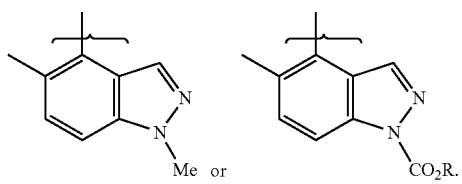
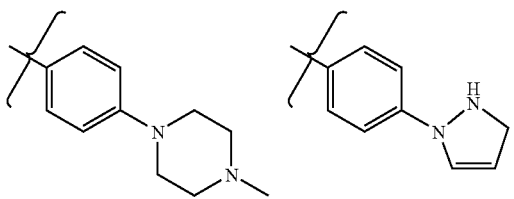

Another class of compounds of special interest are compounds of Formula I as described above in Part 1, in which $R^4$ is —$CONR^6R^7$, —$NHCOR^6$ or —$NHCONR^6R^7$. As noted above, each $R^6$ and $R^7$ is H or an aliphatic, heteroaliphatic, aryl or heteroaryl group, or $NR^6R^7$ is a N-containing heterocyclic or heteroaryl ring or ring system.

In one subset of this class, $R^7$ is H.

In another subset of interest, $R^6$ is a substituted or unsubstituted aryl, heteroaryl or heterocyclic group and may optionally bear one or more aliphatic, heteroaliphatic, aryl, or heteroaryl substituents, each of which may also bear one or more halo, aliphatic, heteroaliphatic, aryl, heteroaryl or other permitted substituents as described below.

This class thus includes compounds in which $R^4$ provides a "Ring B" linked to the "Ring A" through a substituted or unsubstituted amide or urea linkage. This class includes among others compounds of Formula III:

III

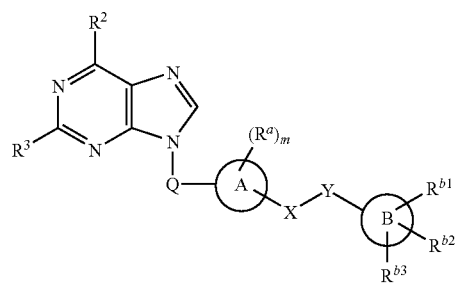

in which X—Y is —$CONR^7$—, —NHCO— or —NHCONR^7—; Ring B is a substituted or unsubstituted aryl, heteroaryl or heterocyclic group bearing one or more optional substituents, $R^{b1}$, $R^{b2}$, $R^{b3}$, etc., selected from those substituents permitted on aryl or heteroaryl rings; and the remaining variables are as defined previously.

Illustrative examples of Ring B systems include aryl, heteroaryl and heterocyclic groups containing one or more optional substituents permitted for such ring systems, such as halo, trihaloalkyl or substituted or unsubstituted aryl, heteroaryl or heterocyclic moieties, as illustrated in part by Ring B systems such as those drawn below:

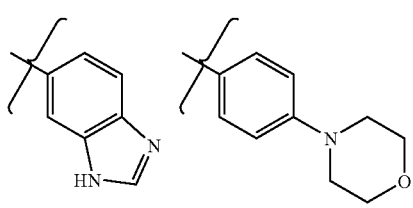

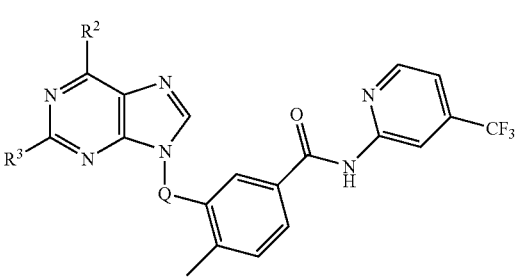

Illustrative examples of this class include compounds of the following formulas:

III(a)

III(b)
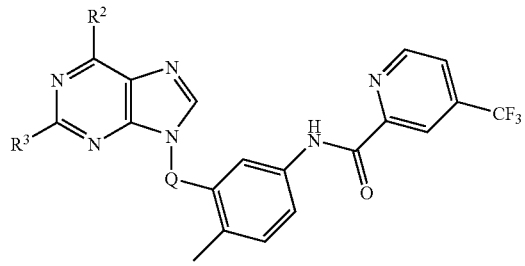

III(c)
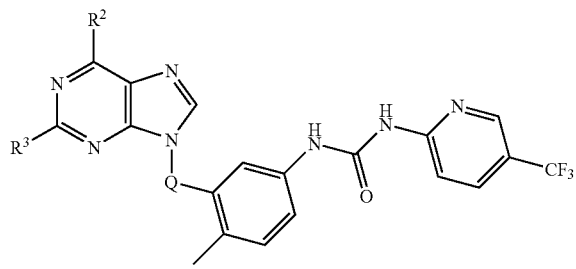

III(d)
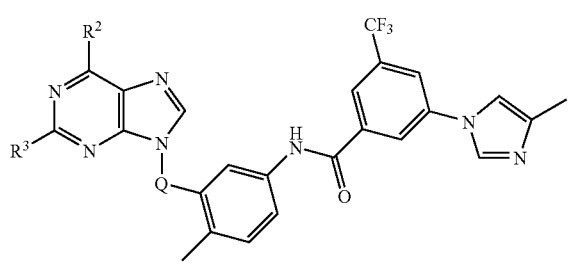

III(e)
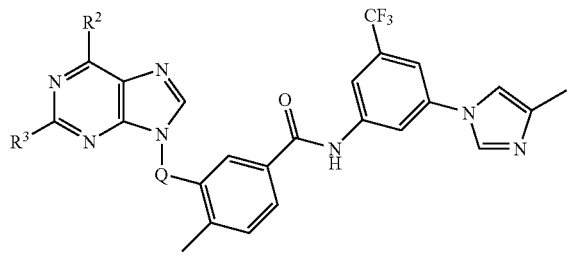

III(f)
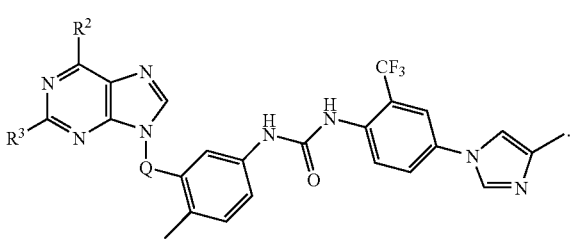

in which the variable groups are as defined above and several illustrative [Ring A]-X—Y-[Ring B] moieties are depicted.

This class also includes compounds in which $R^4$ is —$CONR^6R^7$ or —$NHCONR^6R^7$ where $NR^6R^7$ is a N-containing heterocyclic or heteroaryl ring system, C, as depicted below in Formula IV:

(IV)
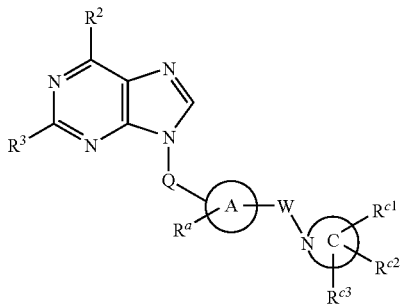

bearing one or more optional substituents, $R^{c1}$, $R^{c2}$, $R^{c3}$, etc., selected from those substituents permitted for an aryl or heteroaryl ring; W is —CO— or —NHCO—; and the remaining variables are as defined previously, as illustrated by the following:

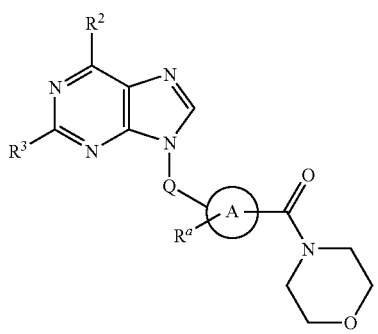

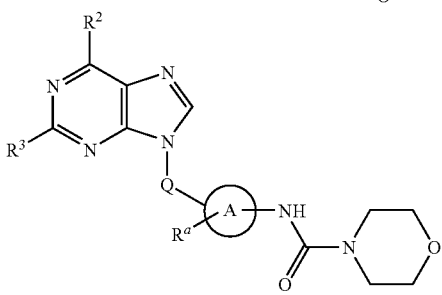

Compounds of interest include among others, compounds of the foregoing classes, subsets and formulas in which $R^3$ is H. Compounds of Formulas III and IV in which $R^3$ is H are of particular interest.

Also of interest are compounds of the foregoing classes, subsets and formulas in which $R^3$ is halogen, especially, F.

Also of interest are compounds of the foregoing classes, subsets and formulas in which $R^3$ is R, including, among others, cases in which $R^4$ is H.

Also of interest are compounds of the foregoing classes, subsets and formulas in which $R^3$ is OR, including, among others, cases in which $R^4$ is H.

Also of interest are compounds of the foregoing classes, subsets and formulas in which $R^3$ is NRR', including, among others, cases in which $R^4$ is H.

Of special interest also, are compounds of each of those five types (i.e., in which $R^3$ is H; $R^3$ is halo; $R^3$ is R; $R^3$ is OR; or $R^3$ is NRR'), as well as compounds of the other classes, subclasses and formulas, in which $R^2$ is R (especially H), halo (especially F), —NRR'(especially —NHR where R is an aliphatic or heteroaliphatic group, including a cyclic group such as a 3-7 carbon cycloaliphatic group or a corresponding acyclic group, which in either case may be substituted or unsubstituted). Illustrative, non-limiting, examples in which $R^2$ is —NHR are illustrated below:

V(a)

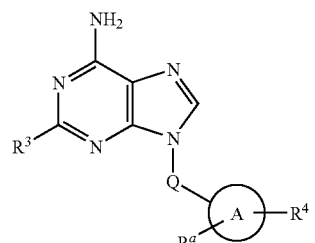

V(b)

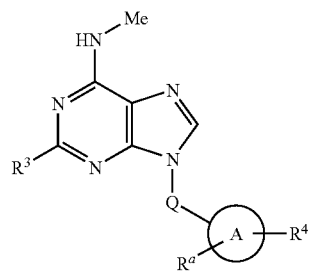

V(c)

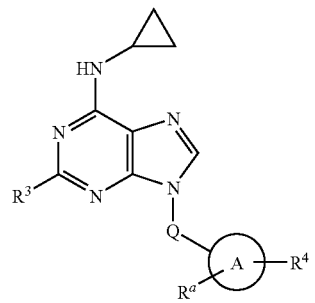

V(d)

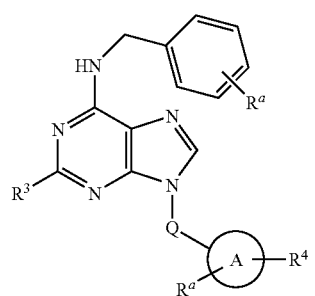

Also of interest are the corresponding compounds in which $R^2$ is H, F or —NHR where R is an aryl or heteroaryl group which may be substituted or unsubstituted, as illustrated below.

VI(a)

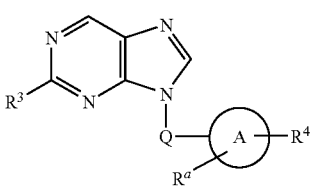

VI(b)

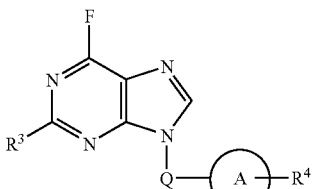

VI(c)

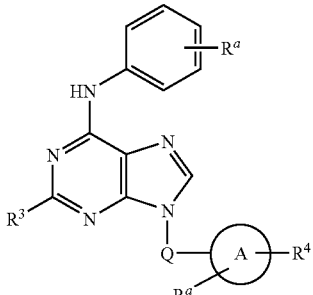

VI(d)

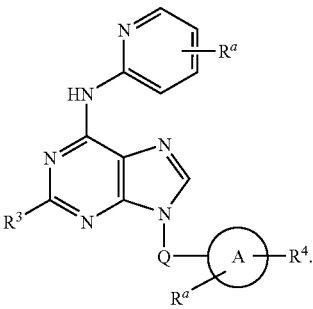

In all of the foregoing cases, Q is either the acetylenic moiety, —CC—, or is a substituted or unsubstituted vinyl moiety —CRCR'— which may be in cis- or trans-orientation or may be represented by a cis-/trans-mixture.

Illustrative examples of compound of Formula VI(c) include, among others, the following:

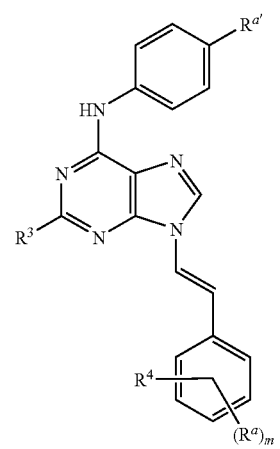

where, for instance, $R^{a'}$ is —PO(Me)$_2$, —SO$_2$R (e.g., —SO$_2$Me), or —SO$_2$NR$^6$R$^7$. One non-limiting example of a phenyl ring bearing substituents $R^4$ and $R^a$ is 1,5-dimethylphenyl. In other cases, $R^4$ is H, or $R^4$ and $(R^a)_m$ (as well as $R^3$) are selected from the full range of candidate substituents for those variables.

Compounds of this invention of particular interest include those with one or more of the following characteristics:
- a molecular weight of less than 1000, preferably less than 800 and more preferably less than 650 mass units (not including the weight of any solvating or co-crystallizing species, of any counter-ion in the case of a salt, or of a moiety added to form a prodrug or other pharmaceutical acceptable derivative); or
- inhibitory activity against a wild type or mutant (especially a clinically relevant mutant) kinase, especially a Src family kinase such as Src, Yes, Lyn or Lck; a VEGF-R such as VEGF-R1 (Flt-1), VEGF-R2 (kdr), or VEGF-R3; a PDGF-R; an Abl kinase or another kinase of interest with an IC50 value of 1 µM or less (as determined using any scientifically acceptable kinase inhibition assay), preferably with an IC50 of 500 nM or better, and optimally with an IC50 value of 250 nM or better; or
- inhibitory activity against a given kinase with an IC50 value at least 100-fold lower than their IC50 values for other kinases of interest; or
- inhibitory activity against both Src and kdr with a 1 µM or better IC50 value against each; or
- a cytotoxic or growth inhibitory effect on cancer cell lines maintained in vitro, or in animal studies using a scientifically acceptable cancer cell xenograft model, (especially preferred are compounds of the invention which inhibit proliferation of cultured K562 cells with a potency at least as great as Gleevec, preferably with a potency at least twice that of Gleevec, and more preferably with a potency at least 10 times that of Gleevec as determined by comparative studies.); or
- a structure in which Q is a vinyl group in the trans-orientation; or
- a structure in which $R^3$ is H or halo and $R^4$ includes a B or C ring.

Also provided is a composition comprising at least one of the disclosed compounds or a pharmaceutical acceptable derivative thereof and at least one pharmaceutically acceptable excipient or additive. Such compositions can be administered to a subject in need thereof to inhibit the growth, development and/or metastasis of cancers, including solid tumors (e.g., breast, colon, pancreatic, CNS and head and neck cancers, among others) and various forms of leukemia, including leukemias and other cancers which are resistant to other treatment, including those which are resistant to treatment with Gleevec or another kinase inhibitor, and generally for the treatment and prophylaxis of diseases or undesirable conditions mediated by one or more kinases which are inhibited by a compound of this invention.

The cancer treatment method of this Invention involves administering (as a monotherapy or in combination with one or more other anti-cancer agents, one or more agents for ameliorating side effects, radiation, etc) a therapeutically effective amount of a compound of the invention to a human or animal in need of it in order to inhibit, slow or reverse the growth, development or spread of cancer, including solid tumors or other forms of cancer such as leukemias, in the recipient. Such administration constitutes a method for the treatment or prophylaxis of diseases mediated by one or more kinases inhibited by one of the disclosed compounds or a pharmaceutically acceptable derivative thereof. "Administration" of a compound of this invention encompasses the delivery to a recipient of a compound of the sort described herein, or a prodrug or other pharmaceutically acceptable derivative thereof, using any suitable formulation or route of administration, as discussed herein. Typically the compound is administered one or more times per week, e.g. daily, every other day, 5 days/week, etc. Oral and intravenous administration are of particular current interest.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue (MW>300) thereof. Pharmaceutically acceptable derivatives thus include among others pro-drugs. A pro-drug is a derivative of a compound, usually with significantly reduced pharmacological activity, which contains an additional moiety which is susceptible to removal in vivo yielding the parent molecule as the pharmacologically active species. An example of a pro-drug is an ester which is cleaved in vivo to yield a compound of interest. Pro-drugs of a variety of compounds, and materials and methods for derivatizing the parent compounds to create the pro-drugs, are known and may be adapted to the present invention.

Particularly favored derivatives and prodrugs of a parent compound are those derivatives and prodrugs that increase the bioavailability of the compound when administered to a mammal (e.g., by permitting enhanced absorption into the blood following oral administration) or which enhance delivery to a biological compartment of interest (e.g., the brain or lymphatic system) relative to the parent compound. Preferred prodrugs include derivatives of a compound of this invention with enhanced aqueous solubility or active transport through the gut membrane, relative to the parent compound.

One important aspect of this invention is a method for treating cancer in a subject in need thereof, which comprises administering to the subject a treatment effective amount of a composition containing a compound of this invention. Various cancers which may be thus treated are noted elsewhere herein and include, among others, cancers which are or have become resistant to another anticancer agent such as Gleevec, Iressa, Tarceva or one of the other agents noted herein. Treatment may be provided in combination with one or more other cancer therapies, include surgery, radiotherapy (e.g., gamma-radiation, neutron beam radiotherapy, electron beam radiotherapy, proton therapy, brachytherapy, and systemic radioactive isotopes, etc.), endocrine therapy, biologic response modifiers (e.g., interferons, interleukins, and tumor necrosis factor (TNF) to name a few), hyperthermia, cryotherapy, agents to attenuate any adverse effects (e.g., antiemetics), and other cancer chemotherapeutic drugs. The other agent(s) may be administered using a formulation, route of administration and dosing schedule the same or different from that used with the compound of this invention.

Such other drugs include but not limited to one or more of the following: an anti-cancer alkylating or intercalating agent (e.g., mechlorethamine, chlorambucil, Cyclophosphamide, Melphalan, and Ifosfamide); antimetabolite (e.g., Methotrexate); purine antagonist or pyrimidine antagonist (e.g., 6-Mercaptopurine, 5-Fluorouracil, Cytarabile, and Gemcitabine); spindle poison (e.g., Vinblastine, Vincristine, Vinorelbine and Paclitaxel); podophyllotoxin (e.g., Etoposide, Irinotecan, Topotecan); antibiotic (e.g., Doxorubicin, Bleomycin and Mitomycin); nitrosourea (e.g., Carmustine, Lomustine); inorganic ion (e.g., Cisplatin, Carboplatin, Oxaliplatin or oxiplatin); enzyme (e.g., Asparaginase); hormone (e.g., Tamoxifen, Leuprolide, Flutamide and Megestrol); mTOR inhibitor (e.g., Sirolimus (rapamycin), Temsirolimus (CCI779), Everolimus (RAD001), AP23573 or other compounds disclosed in PCT/US03/03030 or U.S. Ser. No. 10/357,152, etc.); proteasome inhibitor (such as Velcade, another proteasome inhibitor (see e.g., WO 02/096933) or another NF-kB inhibitor, including, e.g., an IkK inhibitor); other kinase inhibitors (e.g., an inhibitor of Src, BRC/Abl, kdr, flt3, aurora-2, glycogen synthase kinase 3 ("GSK-3"), EGF-R kinase (e.g., Iressa, Tarceva, etc.), VEGF-R kinase, PDGF-R kinase, etc); an antibody, soluble receptor or other receptor antagonist against a receptor or hormone implicated in a cancer (including receptors such as EGFR, ErbB2, VEGFR, PDGFR, and IGF-R; and agents such as Herceptin, Avastin, Erbitux, etc.); etc. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference. Examples of other therapeutic agents are noted elsewhere herein and include among others, Zytoprim, alemtuzmab, altretamine, amifostine, nastrozole, antibodies against prostate-specific membrane antigen (such as MLN-591, MLN591RL and MLN2704), arsenic trioxide, bexarotene, bleomycin, busulfan, capecitabine, Gliadel Wafer, celecoxib, chlorambucil, cisplatin-epinephrine gel, cladribine, cytarabine liposomal, daunorubicin liposomal, daunorubicin, daunomycin, dexrazoxane, docetaxel, doxorubicin, Elliott's B Solution, epirubicin, estramustine, etoposide phosphate, etoposide, exemestane, fludarabine, 5-FU, fulvestrant, gemcitabine, gemtuzumab-ozogamicin, goserelin acetate, hydroxyurea, idarubicin, idarubicin, idamycin, ifosfamide, imatinib mesylate, irinotecan (or other topoisomerase inhibitor, including antibodies such as MLN576 (XR11576)), letrozole, leucovorin, leucovorin levamisole, liposomal daunorubicin, melphalan, L-PAM, mesna, methotrexate, methoxsalen, mitomycin C, mitoxantrone, MLN518 or MLN608 (or other inhibitors of the flt-3 receptor tyrosine kinase, PDFG-R or c-kit), itoxantrone, paclitaxel, Pegademase, pentostatin, porfimer sodium, Rituximab (RITUXAN®), talc, tamoxifen, temozolamide, teniposide, VM-26, topotecan, toremifene, 2C4 (or other antibody which interferes with HER2-mediated signaling), tretinoin, ATRA, valrubicin, vinorelbine, or pamidronate, zoledronate or another bisphosphonate.

This invention further comprises the preparation of a compound of any of Formulas I, II(a)-II(c), III, III(a)-III(f), IV, V(a)-V(d) or VI(a)-VI(d), or of any other of the compounds of this invention. The invention also comprises the use of a compound of the invention, or a pharmaceutically acceptable derivative thereof, in the manufacture of a medicament for the treatment either acutely or chronically of cancer (including leukemias and solid tumors, primary or metastatic, including cancers such as noted elsewhere herein and including cancers which are resistant or refractory to one or more other therapies). The compounds of this invention are useful in the manufacture of an anti-cancer medicament. The compounds of the present invention are also useful in the manufacture of a medicament to attenuate or prevent disorders through inhibition of one or more kinases such as Src, kdr, abl. etc.

Other disorders which may be treated with a compound of this invention include metabolic disorders, inflammatory disorders and osteoporosis and other bone disorders. In such cases the compound of this invention may be used as a monotherapy or may be administered in conjunction with administration of another drug for the disorder, e.g., a bisphosphonate in the case of osteoporosis or other bone-related illnesses.

This invention further encompasses a composition comprising a compound of the invention, including a compound of any of the described classes or subclasses, including those of any of the formulas noted above, among others, preferably in a therapeutically-effective amount, in association with a least one pharmaceutically acceptable carrier, adjuvant or diluent.

Compounds of this invention are also useful as standards and reagents for characterizing various kinases, especially but not limited to kdr and Src family kinases, as well as for studying the role of such kinases in biological and pathological phenomena; for studying intracellular signal transduction pathways mediated by such kinases, for the comparative evaluation of new kinase inhibitors; and for studying various cancers in cell lines and animal models.

3. Definitions

In reading this document, the following information and definitions apply unless otherwise indicated. In addition, unless otherwise indicated, all occurrences of a functional group are independently chosen, as the reader is in some cases reminded by the use of a slash mark or prime to indicate simply that the two occurrences may be the same or different (e.g., R', R', R" and V, V', V", etc.).

The term "aliphatic" as used herein includes both saturated and unsaturated (but non-aromatic), straight chain (i.e., unbranched), branched, cyclic, or polycyclic non-aromatic hydrocarbon moieties, which are optionally substituted with one or more functional groups. Unless otherwise specified, alkyl, other aliphatic, alkoxy and acyl groups preferably contain 1-8 (i.e., "C1-C8"), and in many cases 1-6 (i.e., "C1-C6"), contiguous aliphatic carbon atoms. Illustrative aliphatic groups thus include, for example, methyl, ethyl, n-propyl, isopropyl, cyclopropyl, —$CH_2$-cyclopropyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents.

The term "aliphatic" is thus intended to include alkyl, alkenyl, alkynyl, cycloalkyl, and cycloalkenyl moieties.

As used herein, the term "alkyl" includes both straight, branched and cyclic alkyl groups. An analogous convention applies to other generic terms such as "alkenyl", "alkynyl" and the like.

Furthermore, "alkyl", "alkenyl", "alkynyl" and like groups may be substituted or unsubstituted.

"Alkyl" refers to groups usually having one to eight, preferably one to six carbon atoms. For example, "alkyl" may refer to methyl, ethyl, n-propyl, isopropyl, cyclopropyl, butyl, isobutyl, sec-butyl, tert-butyl, cyclobutyl, pentyl, isopentyl tert-pentyl, cyclopentyl, hexyl, isohexyl, cyclohexyl, etc. Illustrative substituted alkyl groups include, but are not limited to, fluoromethyl, difluoromethyl, trifluoromethyl, 2-fluoroethyl, 3-fluoropropyl, hydroxymethyl, 2-hydroxyethyl, 3-hydroxypropyl, benzyl, substituted benzyl, phenethyl, substituted phenethyl, etc.

The term "alkenyl" refers to groups usually having two to eight, often two to six carbon atoms. For example, "alkenyl" may refer to prop-2-enyl, but-2-enyl, but-3-enyl, 2-methylprop-2-enyl, hex-2-enyl, hex-5-enyl, 2,3-dimethylbut-2-enyl, and the like. The term "alkynyl," which also refers to groups having two to eight, preferably two to six carbons, includes, but is not limited to, prop-2-ynyl, but-2-ynyl, but-3-ynyl, pent-2-ynyl, 3-methylpent-4-ynyl, hex-2-ynyl, hex-5-ynyl, etc.

The term "cycloalkyl" as used herein refers specifically to groups having three to 12, preferably three to ten, carbon atoms in a mono-, di- or polycyclic (i.e., ring) structure. Illustrative cycloalkyls include, but are not limited to, cyclopropyl, cyclobutyl, cyclopentyl, cyclohexyl, cycloheptyl, norbornyl and the like, which, as in the case of other aliphatic or heteroaliphatic or heterocyclic moieties, may optionally be substituted.

The term "heteroaliphatic" as used herein refers to aliphatic moieties which contain an oxygen, sulfur, nitrogen, phosphorous or silicon atom in place of one or more carbon atoms. Heteroaliphatic moieties may be branched, unbranched or cyclic and include acyclic moieties such as $CH_3OCH_2CH_2O$— as well as heterocycles such as morpholino, pyrrolidinyl, etc.

"Heterocycle", "heterocyclyl", or "heterocyclic" as used herein refers to non-aromatic ring systems having five to fourteen ring atoms, preferably five to ten, in which one or more ring carbons, preferably one to four, are each replaced by a heteroatom such as N, O, or S. Non-limiting examples of heterocyclic rings include 3-1H-benzimidazol-2-one, (1-substituted)-2-oxo-benzimidazol-3-yl, 2-tetrahydrofuranyl, 3-tetrahydrofuranyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic" whether saturated or partially unsaturated, also refers to rings that are optionally substituted.

The term "aryl" used alone or as part of a larger moiety as in "aralkyl", "aralkoxy", or "aryloxyalkyl", refers to aromatic ring groups having six to fourteen ring atoms, such as phenyl, 1-naphthyl, 2-naphthyl, 1-anthracyl and 2-anthracyl. An "aryl" ring may contain one or more substituents. The term "aryl" may be used interchangeably with the term "aryl ring". "Aryl" also includes fused polycyclic aromatic ring systems in which an aromatic ring is fused to one or more rings. Non-limiting examples of useful aryl ring groups include phenyl, hydroxyphenyl, halophenyl, alkoxyphenyl, dialkoxyphenyl, trialkoxyphenyl, alkylenedioxyphenyl, naphthyl, phenanthryl, anthryl, phenanthro and the like, as well as 1-naphthyl, 2-naphthyl, 1-anthracyl and 2-anthracyl. Also included within the scope of the term "aryl", as it is used herein, is a group in which an aromatic ring is fused to one or more non-aromatic rings, such as in a indanyl, phenanthridinyl, or tetrahydronaphthyl, where the radical or point of attachment is on the aromatic ring.

The term "heteroaryl" as used herein refers to stable heterocyclic, and polyheterocyclic aromatic moieties having 5-14 ring atoms. Heteroaryl groups may be substituted or unsubstituted and may comprise one or more rings. Possible substituents include, among others, any of the previously mentioned substituents. Examples of typical heteroaryl rings include 5-membered monocyclic ring groups such as thienyl, pyrrolyl, imidazolyl, pyrazolyl, furyl, isothiazolyl, furazanyl, isoxazolyl, thiazolyl and the like; 6-membered monocyclic groups such as pyridyl, pyrazinyl, pyrimidinyl, pyridazinyl, triazinyl and the like; and polycyclic heterocyclic ring groups such as benzo[b]thienyl, naphtho[2,3-b]thienyl, thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxalinyl, quinazolinyl, benzothiazole, benzimidazole, tetrahydroquinoline cinnolinyl, pteridinyl, carbazolyl, beta-carbolinyl, phenanthridinyl, acridinyl, perimidinyl, phenanthrolinyl, phenazinyl, isothiazolyl, phenothiazinyl, phenoxazinyl, and the like (see e.g. Katritzky, Handbook of Heterocyclic Chemistry). Further specific examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indolyl, isoindolyl, acridinyl, or benzoisoxazolyl. Heteroaryl groups further include a group in which a heteroaromatic ring is fused to one or more aromatic or nonaromatic rings where the radical or point of attachment is on the heteroaromatic ring. Examples include tetrahydroquinoline, tetrahydroisoquinoline, and pyrido[3,4-d]pyrimidinyl. The term "heteroaryl" also refers to rings that are optionally substituted. The term "heteroaryl" may be used interchangeably with the term "heteroaryl ring" or the term "heteroaromatic".

An aryl group (including the aryl portion of an aralkyl, aralkoxy, or aryloxyalkyl moiety and the like) or heteroaryl group (including the heteroaryl portion of a heteroaralkyl or heteroarylalkoxy moiety and the like) may contain one or more substituents. Examples of suitable substituents on the unsaturated carbon atom of an aryl or heteroaryl group include halogen, —CN, —R, —OR, —S(O)$_n$R, —SO$_2$NRR', —NRR', —(CO)VR, —O(CO)VR, —NR(CO)VR, —S(CO)VR, or —VJ, wherein each occurrence of V is independently-O—, —S—, —NR—, or a chemical bond; —VR thus encompasses —R, —OR, —SR and —NRR' and —(CO)VR encompasses —C(=O)R, —C(=O)OR, and —C(=O)NRR'. Additional substituents include —V—C(=NR)NR'R", —COCOR, —COM$_k$COR (where k is an integer from 0 through 4, and M$_k$ is thus a bond or a 1-4 carbon aliphatic group), —V—P(=O)(V'R)(V"R'), —NO$_2$, —NRSO$_2$R' and —NRSO$_2$NR'R". To illustrate further, substituents in which V is —NR thus include among others, —NRC(=O)R', —NRC(=O)NR', —NRC(=O)OR', and —NRC(=NH)NR'. Note that R substituents may themselves be substituted or unsubstituted (e.g. non-limiting illustrations of an R moiety include -haloalkyl and trihaloalkyl groups such as chloromethyl or trichloromethyl; -alkoxyalkyl such as methoxyethyl-; mono-, di- and tri-alkoxyphenyl; methylenedioxyphenyl or ethylenedioxyphenyl; halophenyl; and alkylamino). Additional illustrative examples include 1,2-methylene-dioxy, 1,2-ethylenedioxy, protected OH (such as acyloxy)), phenyl, substituted phenyl, —O-phenyl, —O-(substituted) phenyl, -benzyl, substituted benzyl, —O-phenethyl (i.e., —OCH$_2$CH$_2$C$_6$H$_5$), —O-(substituted)phenethyl, —C(O)CH$_2$C(O)R, —CO$_2$R, —C(=O)R (i.e., acyl in cases in which R is aliphatic, aroyl in cases in which R is aryl and heteroaroyl in cases in which R is heteroaryl), —C(=O)NRR', —OC(=O)NRR', —C(=NH)NRR', and —OC(=NH)NRR'. Further examples of substituents include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, and haloalkyl groups.

An aliphatic, heteroaliphatic or non-aromatic heterocyclic group may thus also contain one or more substituents. Examples of suitable substituents on such groups include those listed above for the carbon atoms of an aryl or heteroaryl group and in addition include the following substituents for a saturated carbon atom: =O, =S, =NR, =NNRR', =NNH-C(O)R, =NNHCO$_2$R, or =NNHSO$_2$R. Illustrative examples of substituents on an aliphatic, heteroaliphatic or heterocyclic group include amino, alkylamino, dialkylamino, aminocarbonyl, halogen, alkyl, alkylaminocarbonyl, dialkylaminocarbonyl, alkylamlnocarbonyloxy, dialkylaminocarbonyloxy, alkoxy, nitro, cyano, carboxy, alkoxycarbonyl, alkylcarbonyl, hydroxy, haloalkoxy, or haloalkyl groups.

Illustrative substituents on the nitrogen of an aromatic or non-aromatic heterocyclic ring include —R, —NRR', —C(=O)R, —C(=O)OR, —C(=O)NRR', —C(=NR)NR'R", —COCOR, —COMCOR, —CN, —NRSO$_2$R' and —NRSO$_2$NR'R".

Examples of substituents on the aliphatic group or the phenyl ring include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

This invention encompasses only those combinations of substituents and variables that result in a stable or chemically feasible compound. A stable compound or chemically feasible compound is one that has stability sufficient to permit its preparation and detection. Preferred compounds of this invention are sufficiently stable that they are not substantially altered when kept at a temperature of 40° C. or less, in the absence of moisture or other chemically reactive conditions, for at least a week.

Certain compounds of this invention may exist in tautomeric forms, and this invention includes all such tautomeric forms of those compounds unless otherwise specified.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Thus, this invention encompasses each diastereomer or enantiomer substantially free of other isomers (>90%, and preferably >95%, free from other stereoisomers on a molar basis) as well as a mixture of such isomers.

Particular optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound.

Optically active compounds of the invention can be obtained by using active starting materials. These isomers may be in the form of a free acid, a free base, an ester or a salt.

The compounds of this invention can exist in radiolabelled form, i.e., said compounds may contain one or more atoms containing an atomic mass or mass number different from the atomic mass or mass number: ordinarily found in nature. Radioisotopes of hydrogen, carbon, phosphorous, fluorine and chlorine include $^3$H, $^{14}$C, $^{32}$P, $^{35}$S, $^{43}$F and $^{36}$Cl, respectively. Compounds of this invention which contain those radioisotopes and/or other radioisotopes of other atoms are within the scope of this invention. Tritiated, i.e., $^3$H, and carbon-14, i.e., $^{14}$C, radioisotopes are particularly preferred for their ease of preparation and detectability.

Radiolabelled compounds of this invention can generally be prepared by methods well known to those skilled in the art. Conveniently, such radiolabelled compounds can be prepared by carrying out the procedures disclosed herein except substituting a readily available radiolabelled reagent for a non-radiolabelled reagent.

4. Synthetic Overview

The practitioner has a well-established literature of purine chemistry to draw upon, in combination with the information contained in the examples which follow, for guidance on synthetic strategies, protecting groups, and other materials and methods useful for the synthesis of the compounds of this invention, including compounds containing the various choices for the R$^2$, R$^3$ and -Q(RingA)(R$^a$)$_m$(R$^4$) substituents. The following references, and the references cited therein, may be of particular interest: U.S. Pat. Nos. 5,365,886; 5,434,150; 5,565,566; 5,869,468; 6,057,305; 5,444,068; 5,635,525; 5,866,702; 5,962,479; 6,057,326; 5,994,361; 6,110,923; 6,028,076; 6,084,095; and 6,107,300; WO 01/44259, 00/43394, 90/09178, 00/44750, 97/49689, 95/35297, 95/19774, 97/35539, 97/16452, 00/49018, 97/20842, 98/16528, 99/07705, 99/62908 and 00/55161; and EP 155911, 478292, 531597, 853084, 454-427, 778277, 773023, and 882727.

Various synthetic approaches may be used to produce the compounds described herein, including those approaches depicted schematically below. The practitioner will appreciate that protecting groups may be used in these approaches. "Protecting groups", are moieties that are used to temporarily block chemical reaction at a potentially reactive site (e.g., an amine, hydroxy, thiol, aldehyde, etc.) so that a reaction can be carried out selectively at another site in a multifunctional compound. In preferred embodiments, a protecting group reacts selectively in good yield to give a protected substrate that is suitable for the planned reactions; the protecting group should be selectively removable in good yield by readily available, preferably nontoxic reagents that do not unduly attack the other functional groups present; the protecting group preferably forms an readily separable derivative (more preferably without the generation of new stereogenic centers); and the protecting group preferably has a minimum of additional functionality to avoid the complication of further sites of reaction. A wide variety of protecting groups and strategies, reagents and conditions for deploying and removing them are known in the art. See, e.g., "Protective Groups in Organic Synthesis" Third Ed. Greene, T. W. and Wuts, P. G., Eds., John Wiley & Sons, New York: 1999. For additional background information on protecting group methodologies (materials, methods and strategies for protection and deprotection) and other synthetic chemistry transformations useful in producing the compounds described herein, see in R.

Larock, Comprehensive organic Transformations, VCH Publishers (1989); T. W. Greene and P. G. M. Wuts, Protective Groups in Organic Synthesis, 3rd. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995). The entire contents of these references are hereby incorporated by reference.

In addition, one may chose reagents enriched for a desired isotope, e.g. deuterium in place of hydrogen, to create compounds of this invention containing such isotope(s). Compounds containing deuterium in place of hydrogen in one or more locations, or containing various isotopes of C, N, P and O, are encompassed by this invention and may be used, for instance, for studying metabolism and/or tissue distribution of the compounds or to alter the rate or path of metabolism or other aspects of biological functioning.

Several illustrative overall synthetic approaches based on the Heck Reaction and the Horner Reaction, respectively, are illustrated below:

-continued

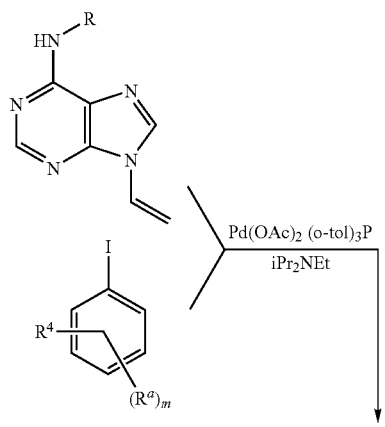

Scheme I:

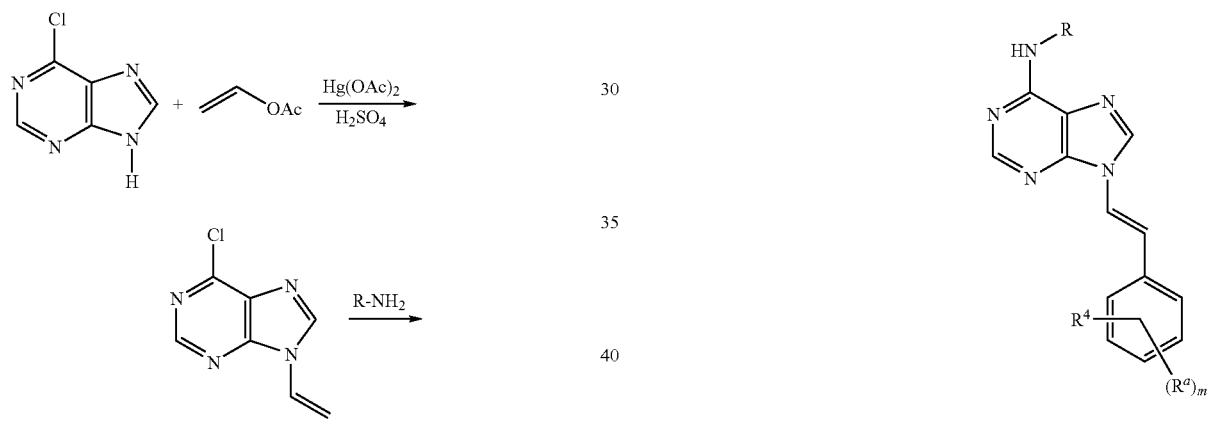

Scheme II:

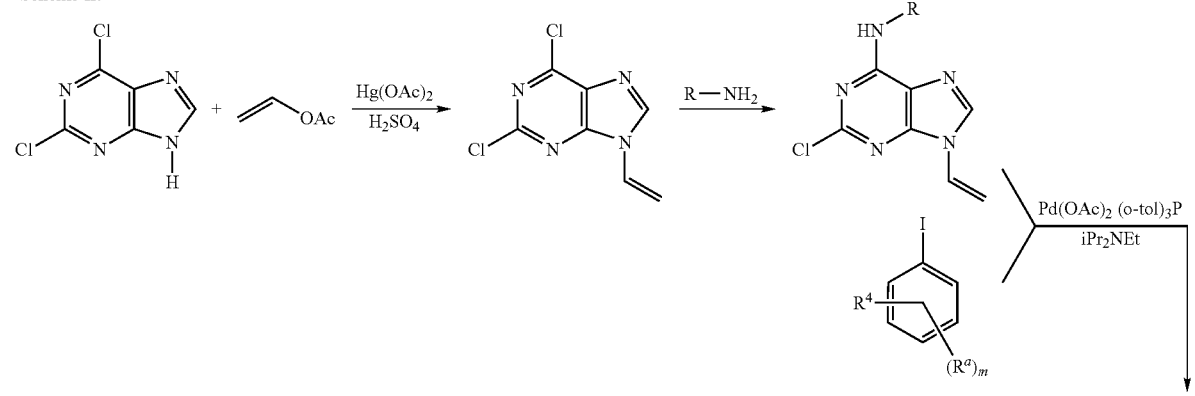

-continued
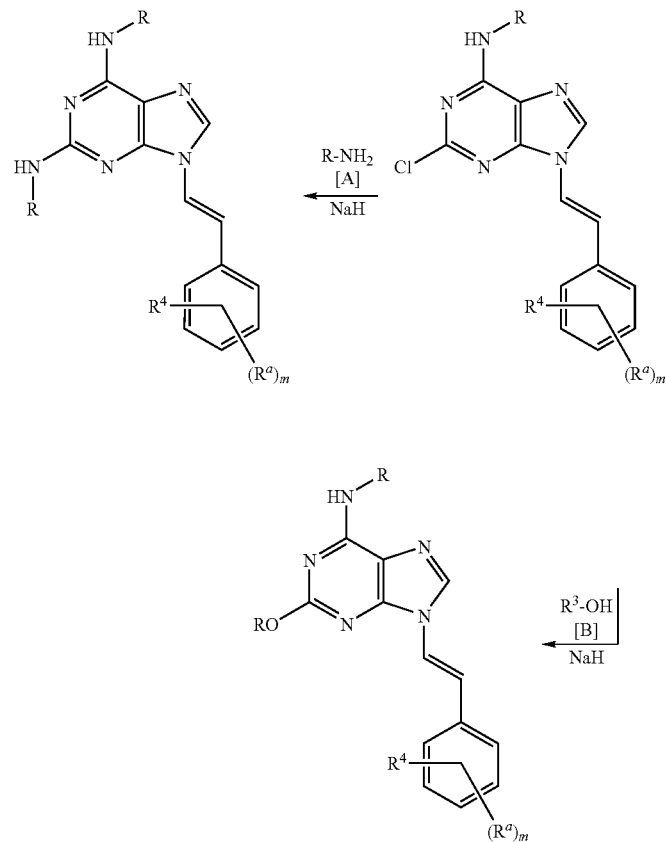
Scheme III:
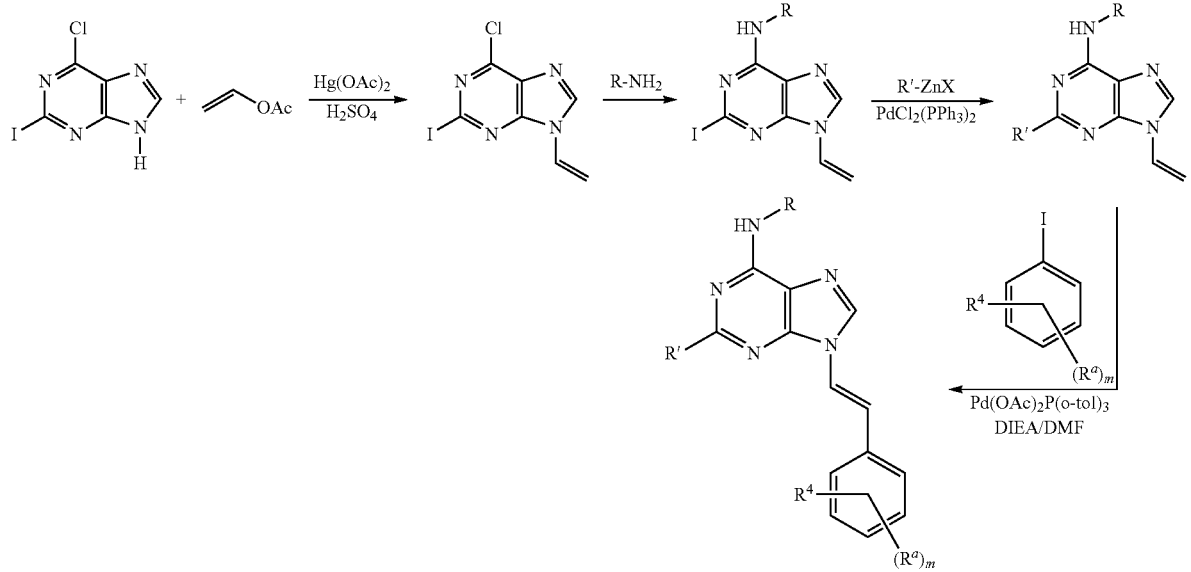
(X = I or Br)

Scheme IV:
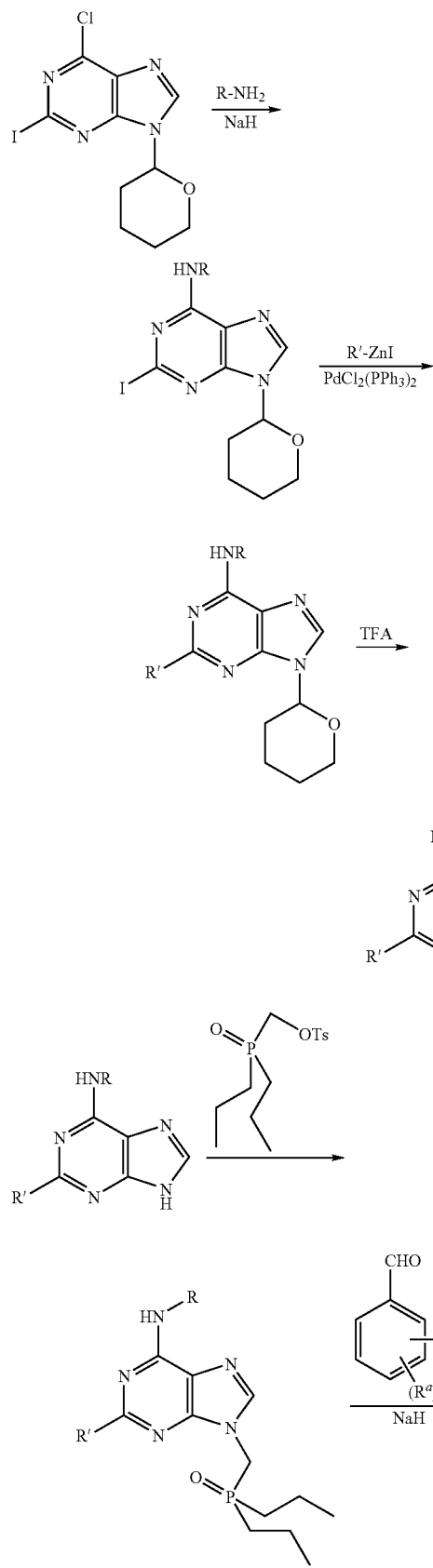
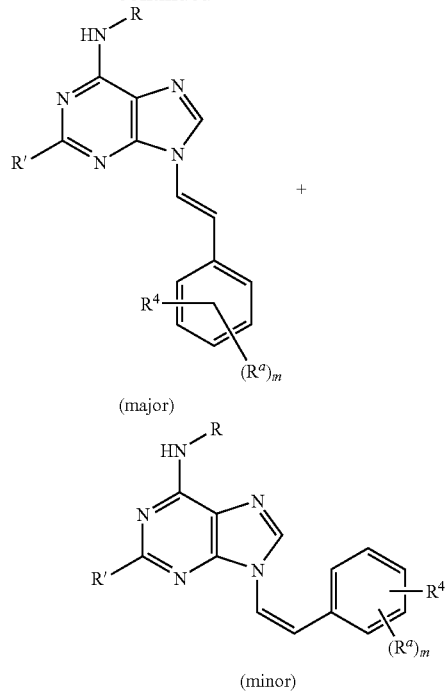
Acetylenic compounds may be prepared using the approach described in J. Chem. Soc. Perkin Trans. 1 1994, 1089:
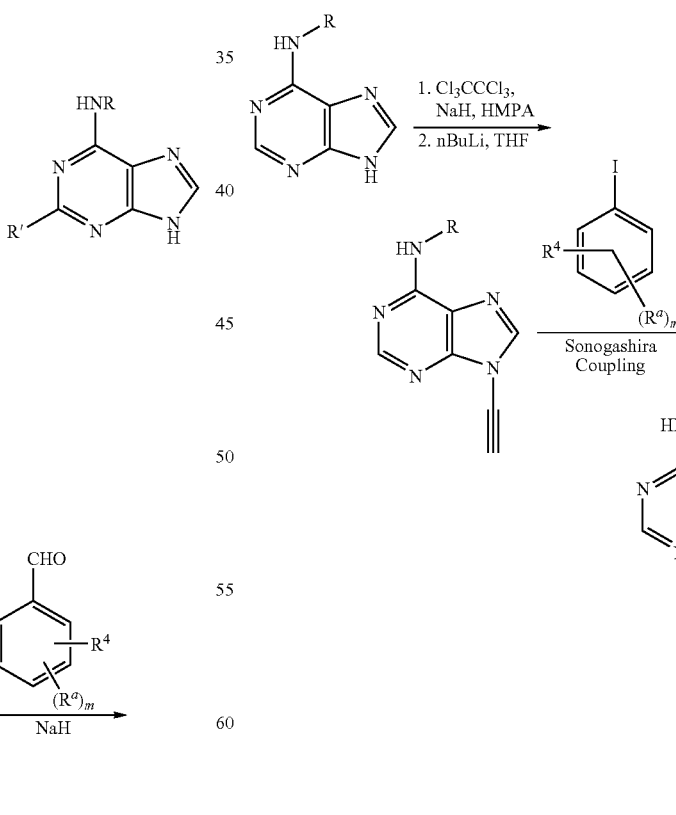
Some illustrative synthetic routes for the preparation of reagents and representative intermediates are presented below:

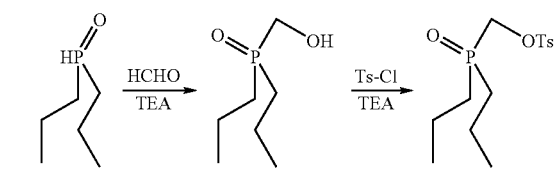

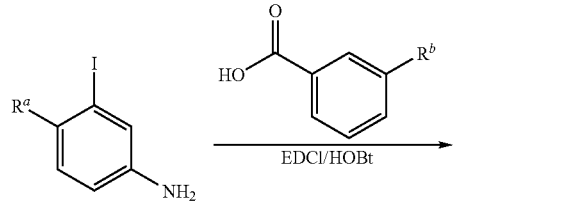

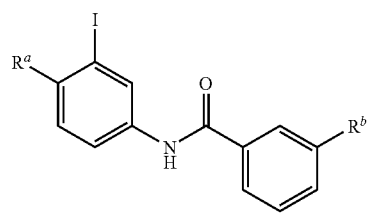

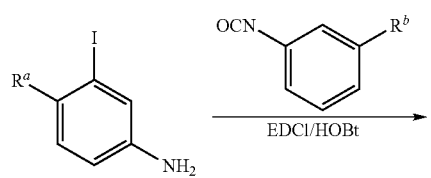

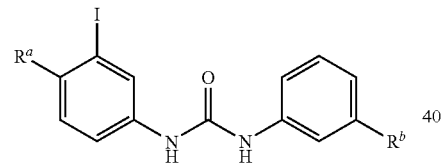

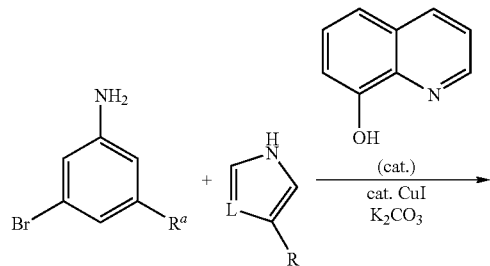

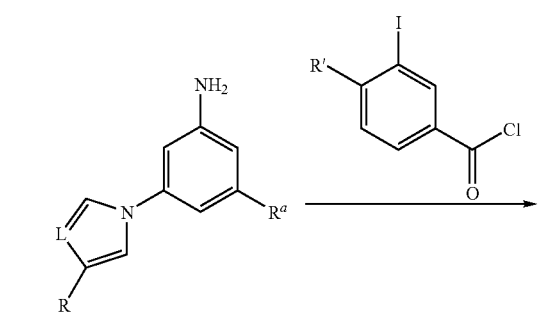

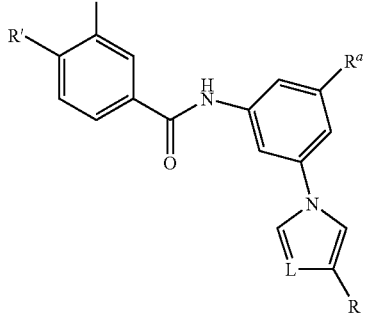

L = N, CH

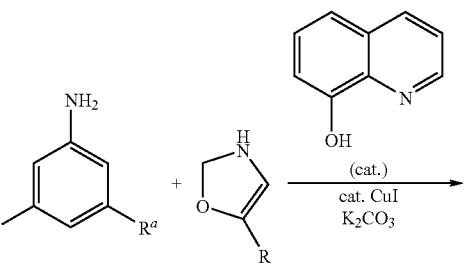

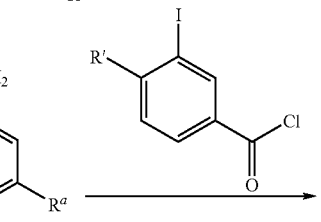

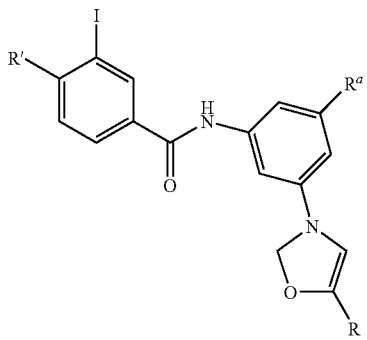

With synthetic approaches such as the foregoing, combined with the examples which follow, additional information provided herein and conventional methods and materials, the practitioner should be able to prepare the full range of compounds disclosed herein.

5. Uses, Formulations, Administration

Pharmaceutical Uses; Indications

This invention provides compounds having biological properties which make them of interest for treating or modulating disease in which kinases may be involved, symptoms of such disease, or the effect of other physiological events mediated by kinases. For instance, a number of compounds of this invention have been shown to inhibit tyrosine kinase activity of Src and abl, among other tyrosine kinases which are believed to mediate the growth, development and/or metastasis of cancer. A number of compounds of the invention have also been found to possess potent in vitro activity against cancer cell lines, including among others K-562 leukemia cells. Observed potencies have been as much as 10-fold more powerful than Gleevec in conventional antiproliferation assays with K562 cells.

Such compounds are thus of interest for the treatment of cancers, including both primary and metastatic cancers, including solid tumors as well as lymphomas and leukemias (including CML, AML and ALL), and including cancers which are resistant to other therapies, including other therapies involving the administration of kinase inhibitors such as Gleevec, Tarceva or Iressa.

Such cancers include, among others, cancers of the breast, cervix, colon and rectum, lung, ovaries, pancreas, prostate, head and neck, gastrointestinal stroma, as well as diseases such as melanoma, multiple myeloma, non-Hodgkin's lymphoma, melanoma, gastric cancers and leukemias (e.g., myeloid, lymphocytic, myelocytic and lymphoblastic leukemias) including cases which are resistant to one or more other therapies, including among others, Gleevec, Tarceva or Iressa.

Resistance to various anticancer agents can arise from one or more mutations in a mediator or effector of the cancer (e.g., mutation in a kinase such as Src or Abl) which correlate with alteration in the protein's drug binding properties, phosphate binding properties, protein binding properties, autoregulation or other characteristics. For example, in the case of BCR-Abl, the kinase associated with chronic myeloid leukemia, resistance to Gleevec has been mapped to a variety of BCR/Abl mutations which are linked to a variety of functional consequences, including among others, steric hindrance of drug occupancy at the kinase's active site, alteration in deformability of the phosphate binding P loop, effects on the conformation of the activation loop surrounding the active site, and others. See e.g. Shah et al, 2002, Cancer Cell 2, 117-125 and Azam et al, 2003, Cell 112, 831-843 and references cited therein for representative examples of such mutations in Bcr/Abl which correlate with drug resistance. See also the following references for additional background information on BCR/Abl, its mechanistic role in CML and drug-resistance-conferring mechanisms and mutations: Kurzrock et al., Philadelphia chromosome-positive leukemias: from basic mechanisms to molecular therapeutics, Ann Intern Med. 2003 May 20; 138(10):819-30; O'Dwyer et al., Demonstration of Philadelphia chromosome negative abnormal clones in patients with chronic myelogenous leukemia during major cytogenetic responses induced by imatinib mesylate. Leukemia. 2003 March; 17(3):481-7; Hochhaus et al., Molecular and chromosomal mechanisms of resistance to imatinib (STI571) therapy, Leukemia. 2002 November; 16(11):2190-6; O'Dwyer et al., The impact of clonal evolution on response to imatinib mesylate (STI571) in accelerated phase CML. Blood. 2002 Sep. 1; 100(5):1628-33; Braziel et al., Hematopathologic and cytogenetic findings in imatinib mesylate-treated chronic myelogenous leukemia patients: 14 months' experience. Blood. 2002 Jul. 15; 100(2):435-41; Corbin et al., Analysis of the structural basis of specificity of inhibition of the Abl kinase by STI571. J Biol. Chem. 2002 Aug. 30; 277(35):32214-9; Wertheim et al., BCR-ABL-induced adhesion defects are tyrosine kinase-independent. Blood. 2002 Jun. 1; 99(11):4122-30;

Kantarjian et al., Hematologic and cytogenetic responses to imatinib mesylate in chronic myelogenous leukemia, N Engl J Med. 2002 Feb. 28; 346(9):645-52. Erratum in: N Engl J Med 2002 Jun. 13; 346(24):1923; Hochhaus et al., Roots of clinical resistance to STI-571 cancer therapy. Science. 2001 Sep. 21; 293(5538):2163; Druker et al., Activity of a specific inhibitor of the BCR-ABL tyrosine kinase in the blast crisis of chronic myeloid leukemia and acute lymphoblastic leukemia with the Philadelphia chromosome. N Engl J Med. 2001 Apr. 5; 344(14):1038-42. Erratum in: N Engl J Med 2001 Jul. 19; 345(3):232; Mauro et al., Chronic myelogenous leukemia. Curr Opin Oncol. 2001 January; 13(1):3-7. Review; Kolibaba et al., CRKL binding to BCR-ABL and BCR-ABL transformation. Leuk Lymphoma. 1999 March; 33(1-2):119-26; Bhat et al., Interactions of p62(dok) with p210(bcr-abl) and Bcr-Abl-associated proteins. J Biol Chem. 1998 Nov. 27; 273(48):32360-8; Senechal et al., Structural requirements for function of the Crk1 adapter protein in fibroblasts and hematopoietic cells. Mol Cell Biol. 1998 September; 18(9):5082-90; Kolibaba et al., Protein tyrosine kinases and cancer. Biochim Biophys Acta. 1997 Dec. 9; 1333(3):F217-48. Review; Heaney et al., Direct binding of CRKL to BCR-ABL is not required for BCR-ABL transformation. Blood. 1997 Jan. 1; 89(1):297-306; Hallek et al., Interaction of the receptor tyrosine kinase p145c-kit with the p210bcr/abl kinase in myeloid cells. Br J Haematol. 1996 July; 94(1):5-16; Oda et al., The SH2 domain of ABL is not required for factor-independent growth induced by BCR-ABL in a murine myeloid cell line. Leukemia. 1995 February; 9(2):295-301; Carlesso et al., Use of a temperature-sensitive mutant to define the biological effects of the p210BCR-ABL tyrosine kinase on proliferation of a factor-dependent murine myeloid cell line. Oncogene. 1994 January; 9(1):149-56.

Again, we contemplate that compounds of this invention, both as monotherapies and in combination therapies, will be useful against leukemias and other cancers which are resistant to one or more other anticancer agents, including among others leukemias and other cancers which are resistant in whole or part to other anticancer agents, specifically including Gleevec and other kinase inhibitors, and specifically including leukemias involving one or more mutations in BCR/Abl, within or outside the kinase domain, including but not limited to those noted in any of the foregoing publications. See in particular Azam et al. and references cited therein for examples of such mutations in BCR/Abl, including, among others, mutations in the drug binding cleft, the phosphate binding P loop, the activation loop, the conserved VAVK of the kinase beta-3 sheet, the catalytic alpha-1 helix of the small N lobe, the long alpha-3 helix within the large C lobe, and the region within the C lobe downstream of the activation loop.

Pharmaceutical Methods

The method of the invention comprises administering to a subject in need thereof a therapeutically effective amount of a compound of the invention.

A "therapeutically effective amount" is that amount effective for detectable killing or inhibition of the growth or spread of cancer cells; the size or number of tumors; or other measure of the level, stage, progression or severity of the cancer. The exact amount required will vary from subject to subject, depending on the species, age, and general condition of the subject, the severity of the disease, the particular anticancer agent, its mode of administration, combination treatment with other therapies, and the like.

The compound, or a composition containing the compound, may be administered using any amount and any route of administration effective for killing or inhibiting the growth of tumors or other forms of cancer.

The anticancer compounds of the invention are preferably formulated in dosage unit form for ease of administration and uniformity of dosage. The expression "dosage unit form" as used herein refers to a physically discrete unit of anticancer agent appropriate for the patient to be treated. As is normally the case, the total daily usage of the compounds and compositions of the present invention will be decided by the attending physician using routine reliance upon sound medical judgment. The specific therapeutically effective dose level for any particular patient or organism will depend upon a variety of factors including the disorder being treated; the severity of the disorder; the potency of the specific compound employed; the specific composition employed; the age, body weight, general health, sex and diet of the patient; the route and schedule of administration; the rate of metabolism and/or excretion of the compound; the duration of the treatment; drugs used in combination or coincident with administration of the compound of this invention; and like factors well known in the medical arts.

Furthermore, after formulation with an appropriate pharmaceutically acceptable carrier in a desired dosage, the compositions of this invention can be administered to humans and other animals orally, rectally, parenterally, intracisternally, intravaginally, intraperitoneally, topically (as by transdermal patch, powders, ointments, or drops), sublingual, bucally, as an oral or nasal spray, or the like.

The effective systemic dose of the compound will typically be in the range of 0.01 to 500 mg of compound per kg of patient body weight, preferably 0.1 to 125 mg/kg, and in some cases 1 to 25 mg/kg, administered in single or multiple doses. Generally, the compound may be administered to patients in need of such treatment in a daily dose range of about 50 to about 2000 mg per patient. Administration may be once or multiple times daily, weekly (or at some other multiple-day interval) or on an intermittent schedule. For example, the compound may be administered one or more times per day on a weekly basis (e.g. every Monday) indefinitely or for a period of weeks, e.g. 4-10 weeks. Alternatively, it may be administered daily for a period of days (e.g. 2-10 days) followed by a period of days (e.g. 1-30 days) without administration of the compound, with that cycle repeated indefinitely or for a given number of repetitions, e.g. 4-10 cycles. As an example, a compound of the invention may be administered daily for 5 days, then discontinued for 9 days, then administered daily for another 5 day period, then discontinued for 9 days, and so on, repeating the cycle indefinitely, or for a total of 4-10 times.

The amount of compound which will be effective in the treatment or prevention of a particular disorder or condition will depend in part on well known factors affecting drug dosage. In addition, in vitro or in vivo assays may optionally be employed to help identify optimal dosage ranges. A rough guide to effective doses may be extrapolated from dose-response curves derived from in vitro or animal model test systems. The precise dosage level should be determined by the attending physician or other health care provider and will depend upon well known factors, including route of administration, and the age, body weight, sex and general health of the individual; the nature, severity and clinical stage of the disease; the use (or not) of concomitant therapies; and the nature and extent of genetic engineering of cells in the patient.

When administered for the treatment or inhibition of a particular disease state or disorder, the effective dosage of the compound of this invention may vary depending upon the particular compound utilized, the mode of administration, the condition, and severity thereof, of the condition being treated, as well as the various physical factors related to the individual being treated. In many cases, satisfactory results may be obtained when the compound is administered in a daily dosage of from about 0.01 mg/kg-500 mg/kg, preferably between 0.1 and 125 mg/kg, and more preferably between 1 and 25 mg/kg. The projected daily dosages are expected to vary with route of administration. Thus, parenteral dosing will often be at levels of roughly 10% to 20% of oral dosing levels.

When the compound of this invention is used as part of a combination regimen, dosages of each of the components of the combination are administered during a desired treatment period. The components of the combination may administered at the same time; either as a unitary dosage form containing both components, or as separate dosage units; the components of the combination can also be administered at different times during a treatment period, or one may be administered as a pretreatment for the other.

Regarding the Compounds

Compounds of present invention can exist in free form for treatment, or where appropriate, as a pharmaceutically acceptable salt or other derivative. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, phosphonates and other types of compounds, are well known in the art. For example, S. M. Berge, et al. describe pharmaceutically acceptable salts in detail in *J. Pharmaceutical Sciences*, 66:1-19 (1977), incorporated herein by reference. The salts can be prepared in situ during the isolation and purification of the compounds of the invention, or separately by reacting the free base or free acid of a compound of the invention with a suitable base or acid, respectively. Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower-alkyl sulfonate and aryl sulfonate.

Additionally, as used herein, the term "pharmaceutically acceptable ester" refers preferably to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyrates, acrylates and ethylsuccinates. Obviously, esters can be formed with a hydroxyl or carboxylic acid group of the compound of the invention.

Furthermore, the term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are transformed in vivo to yield the parent compound of the above formula, for example by hydrolysis in blood. See, e.g., T. Higuchi and V. Stella, Pro-drugs as Novel Delivery Systems, Vol. 14 of the A.C.S. Symposium Series, and Edward B. Roche, ed., Bioreversible Carriers in Drug Design, American Pharmaceutical Association and Pergamon Press, 1987, both of which are incorporated herein by reference.

Compositions

Accordingly, compositions are provided, which comprise any one of the compounds described herein (or a prodrug, pharmaceutically acceptable salt or other pharmaceutically acceptable derivative thereof), and one or more pharmaceutically acceptable carriers or excipients. These compositions optionally further comprise one or more additional therapeutic agents. Alternatively, a compound of this invention may be administered to a patient in need thereof in combination with the administration of one or more other therapeutic regimens (e.g. Gleevec or other kinase inhibitors, interferon, bone marrow transplant, farnesyl transferase inhibitors, bisphosphonates, thalidomide, cancer vaccines, hormonal therapy, antibodies, radiation, etc). For example, additional therapeutic agents for conjoint administration or inclusion in a pharmaceutical composition with a compound of this invention may be another one or more anticancer agents.

As described herein, the compositions of the present invention comprise a compound of the invention together with a pharmaceutically acceptable carrier, which, as used herein, includes any and all solvents, diluents, or other vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition.

Formulations

This invention also encompasses a class of compositions comprising the active compounds of this invention in association with one or more pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly, intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient.

Examples of such dosage units are tablets or capsules. For example, these may contain an amount of active ingredient from about 1 to 2000 mg, preferably from about 1 to 500 mg, more commonly from about 5 to 200 mg. A suitable daily dose for a human or other mammal may vary depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A typical daily dose is in the range of 0.01 to 500 mg of compound per kg body weight, preferably between 0.1 and 125 mg/kg body weight and in some cases between 1 and 25 mg/kg body weight. As mentioned previously, the daily dose can be given in one administration or may be divided between 2, 3, 4 or more administrations.

For therapeutic purposes, the active compounds of this invention are ordinarily combined with one or more adjuvants, excipients or carriers appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropyl methyl cellulose.

In the case of skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at Least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

The compounds of this invention can also be administered by a transdermal device. Preferably transdermal administration will be accomplished using a patch either of the reservoir and porous membrane type or of a solid matrix variety. In either case, the active agent is delivered-continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as diisoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required.

Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients.

The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers.

Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Pharmaceutical compositions of this invention comprise a compound of the formulas described herein or a pharmaceutically acceptable salt thereof; an additional agent selected from a kinase inhibitory agent (small molecule, polypeptide, antibody, etc.), an immunosuppressant, an anticancer agent, an anti-viral agent, antiinflammatory agent, antifungal agent, antibiotic, or an anti-vascular hyperproliferation compound; and any pharmaceutically acceptable carrier, adjuvant or vehicle.

Alternate compositions of this invention comprise a compound of the formulae described herein or a pharmaceutically acceptable salt thereof; and a pharmaceutically acceptable carrier, adjuvant or vehicle. Such compositions may optionally comprise one or more additional therapeutic agents, including, for example, kinase inhibitory agents (small molecule, polypeptide, antibody, etc.), immunosuppressants, anti-cancer agents, anti-viral agents, antiinflammatory agents, antifungal agents, antibiotics, or anti-vascular hyperproliferation compounds.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, selfemulsifying drug delivery systems (SEDDS) such as d-atocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as u-, P-, and y-cyclodextrin, or chemically modified derivatives such as hydroxyalkylcyclodextrins, including 2 and 3-hydroxypropyl-cyclodextrins, or other solubilized derivatives may also be advantageously used to enhance delivery of compounds of the formulae described herein.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents.

If desired, certain sweetening and/or flavoring and/or coloring agents may be added.

The pharmaceutical compositions of this invention may comprise formulations utilizing liposome or microencapsulation techniques, various examples of which are known in the art.

The pharmaceutical compositions of this invention may be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents, examples of which are also well known in the art.

Combinations

While the compounds of the invention can be administered as the sole active pharmaceutical agent, they can also be used in combination with one or more other compounds of the invention or with one or more other agents. When administered as a combination, the therapeutic agents can be formulated as separate compositions that are administered at the same time or sequentially at different times, or the therapeutic agents can be given as a single composition.

The phrase "combination therapy", in referring to the use of a compound of this invention together with another pharmaceutical agent, means the coadministration of each agent in a substantially simultaneous manner as well as the administration of each agent in a sequential manner, in either case, in a regimen that will provide beneficial effects of the drug combination. Coadministration includes inter alia the simultaneous delivery, e.g., in a single tablet, capsule, injection or other dosage form having a fixed ratio of these active agents, as well as the simultaneous delivery in multiple, separate dosage forms for each agent respectively.

Thus, the administration of compounds of the present invention may be in conjunction with additional therapies known to those skilled in the art in the prevention or treatment of cancer, such as radiation therapy or cytostatic agents, cytotoxic agents, other anti-cancer agents and other drugs to ameliorate symptoms of the cancer or side effects of any of the drugs.

If formulated as a fixed dose, such combination products employ the compounds of this invention within the accepted dosage ranges. Compounds of this invention may also be administered sequentially with other anticancer or cytotoxic agents when a combination formulation is inappropriate. The invention is not limited in the sequence of administration; compounds of this invention may be administered prior to, simultaneously with, or after administration of the other anticancer or cytotoxic agent.

Currently, standard treatment of primary tumors consists of surgical excision, when appropriate, followed by either radiation or chemotherapy, typically administered intravenously (IV). The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of cancer by combination drug chemotherapy. And there are several major categories of such antineoplastic agents, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention includes antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, CibaGeigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Welcome EHNA, Merck & Co.

EX-015, fazarabine, floxuridine, fludarabine phosphate, 5-fluorouracil, N-(21-furanidyl) fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC788, thioguanine, tiazofurin, Erbamont TIF, trimetrexate, tyrosine kinase inhibitors, Talho UFT and uricytin.

A second family of antineoplastic agents which may be used in combination with compounds of the present invention consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D 384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G M, Chinoin GYKI-17230, hepsulfam, ifosfamide, iproplatin, lomustine, mafosfamide, mitolactolf Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN II, Ajinomoto AN3, Nippon Soda anisomycins, anthracycline, azino-mycin-A, bisucaberin, Bristol-Myers BL-6859, Bristol-Myers BMY-25067, Bristol-Myers BNY-25551, Bristol-Myers BNY-26605 IBristolMyers BNY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko, DC89-AI, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-Al, esperamicin-Alb, Erbamont FCE21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of (α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5. antineoplaston AS2-1F Henkel APD, aphidicolin glycinate, asparaginase, Avarol, baccharin, batracylin, benfluoron, benzotript, Ipsen-Beaufour BIM-23015, bisantrene, BristoMyers BNY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, WarnerLambert CI-937, Warner-Lambert CI-941, Warner-Lambert CI958, clanfenur, claviridenone, ICN compound 1259, ICN compound 4711, Contracan, Yakult Honsha CPT-11, crisnatol, curaderm, cytochalasin B. cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704t gallium nitrate, genkwadaphnin, Chugai GLA-43, Glaxo GR-63178, grifolan NMF5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU 1121 Lilly LY-186641, NCI (US) MAP, marycin, Merrel Dow MDL-27048, Medco MEDR-340, merbarone, merocyanlne derivatives, methylanilinoacridine, Molecular Genetics MG1136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, WarnerLambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, and withanolides. Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-NI, interferon alfa-n3, interferon alfacon1, interferon alpha, natural, interferon beta, interferon beta-Ia, interferon beta-Ib, interferon gamma, natural interferon gamma-Ia, interferon gamma-Ib, interleukin-I beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama. vaccine, melanoma lysate vaccine, valrubicin, verteporfin, vinorelbine, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinidel filgrastim SDO1 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM iodine 131 MAb (Techniclone), polymorphic epithelial mucin-yttrium 90 MAb (Antisoma), marimastat, menogaril, mitumomab, motexafin, gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN)y SU 6668 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Treatment Kits

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the substituted purine dosages, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

The following representative examples contain important additional information, exemplification and guidance which can be adapted to the practice of this invention in its various embodiments and the equivalents thereof. These examples are intended to help illustrate the invention, and are not intended to, nor should they be construed to, limit its scope. Indeed, various modifications of the invention, and many further embodiments thereof, in addition to those shown and described herein, will become apparent to those skilled in the art upon review of this document, including the examples which follow and the references to the scientific and patent literature cited herein. The contents of those cited references are incorporated herein by reference to help illustrate the state of the art. In addition, for purposes of this invention, the chemical elements are identified in accordance with the Periodic Table of the Elements, CAS version, Handbook of Chemistry and Physics, 75$^{th}$ Ed., inside cover. Additionally, general principles of organic chemistry, as well as specific functional moieties and reactivity, are described in "Organic Chemistry", Thomas Sorrell, University Science Books, Sausalito: 1999, and "Organic Chemistry", Morrison & Boyd (3d Ed), the entire contents of both of which are incorporated herein by reference.

EXAMPLES

Example 1

(E)-N-(4-methyl-3-(2-(6-(methylamino)-9H-purin-9-yl)vinyl)phenyl)-3-(trifluoromethyl)benzamide A) N-Methyl-9-vinyl-9H-purin-6-amine 6-Chloro-9-vinylpurine (JOC 1968, 33, 1341) (0.54 g, 3 mmol), was added to methylamine (15 mmol, 2.0M in THF) in THF (5 mL) and the mixture was stirred for 5 h at rt. Water was added to dissolve the white precipitate (methylamine hydrochloride). The aqueous layer was extracted with ethyl acetate and the combined organic layers were dried over sodium sulfate, concentrated on a rotavap, and then subjected to silica gel column chromatography (5% methanol/methylene chloride) yielding the desired product.

B) N-(3-Iodo-4-methylphenyl)-3-(trifluoromethyl)benzamide

A solution of 3-iodo-4-methylaniline (1.22 g, 5.25 mmol), 3-(trifluoromethyl)benzoic acid (0.95 g, 5 mmol), HOBt (0.68 g, 5 mmol), and EDCI (1.05 g, 5.5 mmol) in THF (20 mL) was stirred overnight at rt. Water was added and the aqueous layer was extracted with dichloromethane. The combined organic layers were dried over sodium sulfate, concentrated on a rotavap, and then subjected to silica gel column chromatography (3:1 hexane/ethyl acetate) yielding the desired product.

C) (E)-N-(4-Methyl-3-(2-(6-(methylamino)-9H-purin-9-yl)vinyl)phenyl)-3-(trifluoromethyl)benzamide A pressure tube was charged with N-methyl-9-vinyl-9H-purin-6-amine (0.088 g, 0.5 mmol), N-(3-iodo-4-methylphenyl)-3-(trifluoromethyl)benzamide (0.20 g, 0.5 mmol), palladium acetate (0.05 eq), tri-(o-tolyl)phosphine (0.1 eq), and DMF (2 ml). The resulting solution was degassed by bubbling $N_2$ for 10 minutes. N,N-Diisopropylethylamine (0.19 g, 1.5 mmol) was added and this solution was stirred at 110° C. for 15 h. Water was added and the aqueous layer was extracted with ethyl acetate. The combined organic layers were dried over sodium sulfate, concentrated on a rotavap, and then subjected to silica gel column chromatography (5% methanol/methylene chloride) yielding the desired product: MS [M+H]$^+$ 453; m.p. 201° C.

Example 2

N-(4-Methyl-3-(2-(6-(methylamino)-9H-purin-9-yl)ethyl)phenyl)-3-(trifluoromethyl)benzamide To a solution of (E)-N-(4-methyl-3-(2-(6-(methylamino)-9H-purin-9-yl)vinyl)phenyl)-3-(trifluoromethyl)benzamide (0.10 g) in MeOH was added a catalytic amount of 10% palladium on carbon. The resulting mixture was hydrogenated under 50 psi $H_2$ for 48 h at which point HPLC indicated completion. The catalyst was removed by filtration and the filtrate was concentrated on a rotavap and further dried under vacuum yielding the desired product.

Example 3

(E)-N-(3-(2-(6-(4-(Dimethylphosphoryl)phenylamino)-9H-purin-9-yl)vinyl)-4-methylphenyl)-3-(trifluoromethyl)benzamide A) N-(4-(Dimethylphosphoryl)phenyl)-9-vinyl-9H-purin-6-amine A mixture of 6-chloro-9-vinylpurine (0.18 g, 1 mmol), 4-dimethylphosphinylaniline (0.17 g, 1 mmol), and pyridine hydrochloride (0.11 g, 1 mmol) was dissolved in 2-ethoxyethanol (2 mL). The resulting solution was heated at 160° C. for 10 minutes under microwave irradiation. The mixture was concentrated to dryness on a rotavap. EtOAc and aq. NaHCO$_3$ were added. The aqueous layer was extracted with ethyl acetate and the combined organic layers were dried over sodium sulfate, concentrated on a rotavap, and then subjected to silica gel column chromatography (eluent: 10% methanol/methylene chloride) yielding the desired product.

B) (E)-N-(3-(2-(6-(4-(Dimethylphosphoryl)phenylamino)-9H-purin-9-yl)vinyl)-4-methylphenyl)-3-(trifluoromethyl)benzamide The titled compound was made as for example 1 using N-(4-(dimethylphosphoryl)phenyl)-9-vinyl-9H-purin-6-amine and N-(3-iodo-4-methylphenyl)-3-(trifluoromethyl)benzamide: MS [M+H]$^+$ 591; m.p. 230-234° C.

Example 4

(E)-3-(2-(6-(Cyclopropylamino)-9H-purin-9-yl)vinyl)-4-methyl-N-(3-(4-methyl-1-imidazol-1-yl)-5-(trifluoromethyl)phenyl)benzamide A) N-cyclopropyl-9-vinyl-9H-purin-6-amine 6-Chloro-9-vinylpurine (0.54 g, 3 mmol) was mixed with cyclopropylamine (1.71 g, 30 mmol) in THF (10 mL) and the mixture was stirred for 5 h at rt. Water was added to dissolve the white precipitate (cyclopropylamine hydrochloride). The aqueous layer was extracted with ethyl acetate and the combined organic layers were dried over sodium sulfate, concentrated on a rotavap, and then recrystallized from EtOAc/hexanes yielding the desired product.

B) 3-(4-Methyl-1H-imidazol-1-yl)-5-(trifluoromethyl)benzenamine

A suspension of 3-bromo-5-(trifluoromethyl)aniline (4.80 g, 20 mmol), 4-methylimidazole (1.97 g, 24 mmol), potassium carbonate (3.04 g, 22 mmol), CuI (0.57 g, 3 mmol), and 8-hydroxyquinoline (0.44 g, 3 mmol) in dry DMSO (20 mL) in a pressure tube was degassed by bubbling $N_2$ into the suspension for 10 minutes while stirring. The tube was sealed tightly. The mixture was heated at 120° C. (oil bath temperature) for 15 h. The mixture was cooled down to 45-50° C. and 14% aq. NH$_4$OH (20 mL) was added. The mixture was maintained at this temperature for 1 h. After cooling to rt, water and ethyl acetate were added. The aqueous layer was extracted with ethyl acetate and the combined organic layers were passed through a short silica gel column to remove most of green/blue Cu salt. The filtrate was dried over sodium sulfate and concentrated on a rotavap. The crude product was recrystallized from EtOAc/hexanes, giving pure pale yellow needles. The mother liquor was concentrated and the residue was purified on silica gel column (5% methanol/methylene chloride), yielding a second crop as pale yellow needles.

C) 3-iodo-4-methyl-N-(3-(4-methyl-1H-imidazol-1-yl)-5-(trifluoromethyl)phenyl)benzamide 3-iodo-4-methylbenzoic acid (2.62 g, 10 mmol) was refluxed in SOCl$_2$ (10 mL) for 1 h. The volatile components were removed on a rotavap and the residue was dissolved in benzene (10 mL), concentrated to dryness on a rotavap and further dried under vacuum. The resulting acyl chloride was added to a solution 3-(4-methyl-1H-imidazol-1-yl)-5-(trifluoromethyl)benzenamine (2.46 g, 10.2 mmol), N,N-diisopropylethylamine (1.56 g, 12 mmol), and a catalytic amount of DMAP in THF (20 mL). After stirring at rt for 2 h, the reaction was quenched with water. EtOAc was added and the layers separated. The combined organic layers were concentrated to dryness and used without purification in next step.

D) (E)-3-(2-(6-(Cyclopropylamino)-9H-purin-9-yl) vinyl)-4-methyl-N-(3-(4-methyl-1-imidazol-1-yl)-5-(trifluoromethyl)phenyl)benzamide The titled compound was made as for example 1 using 3-iodo-4-methyl-N-(3-(4-methyl-1H-imidazol-1-yl)-5-(trifluoromethyl)phenyl)benzamide and N-cyclopropyl-9-vinyl-9H-purin-6-amine: MS [M+H]$^+$ 559; m.p. 225-227° C.

Example 5

(E)-3-(2-(6-(Cyclopropylamino)-9H-purin-9-yl)vinyl)-4-methyl-N-(3-(trifluoromethyl)phenyl)benzamide The titled compound was made as for example 4 using 3-iodo-4-methyl-N-(3-(trifluoromethyl)phenyl)benzamide and N-cyclopropyl-9-vinyl-9H-purin-6-amine: MS [M+H]$^+$ 479; m.p. 201° C.

Example 6

(E)-1-(3-(2-(6-(Cyclopropylamino)-9H-purin-9-yl) vinyl)-4-methylphenyl)-3-(3-(trifluoromethyl)phenyl)urea A) 1-(3-Iodo-4-methylphenyl)-3-(3-(trifluoromethyl) phenyl)urea A mixture of 3-iodo-4-methylaniline (1.17 g, 5 mmol) and 3-(trifluoromethyl)-phenylisocyanate (1.03 g, 5.5 mmol) was stirred at rt for 4 h. Filtration (ethyl acetate wash) yielded the desired product.

B) (E)-1-(3-(2-(6-(Cyclopropylamino)-9H-purin-9-yl)vinyl)-4-methylphenyl)-3-(3-(trifluoromethyl) phenyl)urea The titled compound was made as for example 4 using 1-(3-iodo-4-methylphenyl)-3-(3-(trifluoromethyl)phenyl) urea and N-cyclopropyl-9-vinyl-9H-purin-6-amine: MS [M+H]$^+$ 494; m.p. 160-162° C.

Example 7

(E)-3-(2-(6-(Cyclopropylamino)-9H-purin-9-yl)vinyl)-4-methyl-N-(4-(trifluoromethyl)pyridin-2-yl) benzamide A) 3-Iodo-4-methyl-N-(4-(trifluoromethyl)pyridin-2-yl)benzamide The titled compound was made as for example 4C, using 2-amino-4-(trifluoromethyl)pyridine instead of 3-(4-methyl-1H-imidazol-1-yl)-5-(trifluoromethyl)benzenamine. This acylation reaction gave significant amounts of bis-acylated product, which is slightly less polar by TLC and was converted to the desired mono-acylated product by treatment with 4N aq. NaOH at 50° C. for 30 minutes then worked up as for example 4.

B) (E)-3-(2-(6-(Cyclopropylamino)-9H-purin-9-yl) vinyl)-4-methyl-N-(4-(trifluoromethyl)pyridin-2-yl) benzamide The titled compound was made as for example 4 using 3-iodo-4-methyl-N-(4-(trifluoromethyl)pyridin-2-yl)benzamide and N-cyclopropyl-9-vinyl-9H-purin-6-amine: MS [M+H]$^+$ 480; m.p. 232° C.

Example 8

(E)-3-(2-(6-Amino-9H-purin-9-yl)vinyl)-4-methyl-N-(3-(4-methyl-1H-imidazol-1-yl)-5-(trifluoromethyl)phenyl)benzamide A) 9-Vinyl-9H-purin-6-amine 6-Chloro-9-vinylpurine (0.48 g, 3 mmol) was added to saturated ammonia/methanol (20 mL) and the mixture was heated at 50° C. for 15 h. Water was added and the aqueous layer was extracted with ethyl acetate. The combined organic layers were dried over sodium sulfate, concentrated on a rotavap then subjected to silica gel column chromatography (5% methanol/methylene chloride) yielding the desired product.

B) (E)-3-(2-(6-Amino-9H-purin-9-yl)vinyl)-4-methyl-N-(3-(4-methyl-1H-imidazol-1-yl)-5-(trifluoromethyl)phenyl)benzamide The titled compound was made as for example 4 using 3-iodo-4-methyl-N-(3-(4-methyl-1 W-imidazol-1-yl)-5-(trifluoromethyl)phenyl)benzamide and 9-vinyl-9H-purin-6-amine: MS [M+H]$^+$ 519; m.p. 258° C.

Example 9

(E)-N-(4-Methyl-3-(2-(6-(pyridin-3-ylamino)-9H-purin-9-yl)vinyl)phenyl)-3-(trifluoromethyl)benzamide A) (E)-N-(3-(2-(6-Chloro-9H-purin-9-yl)vinyl)-4-methylphenyl)-3-(trifluoromethyl)benzamide The titled compound was made as for example 1C using 6-chloro-9-vinylpurine and N-(3-iodo-4-methylphenyl)-3-(trifluoromethyl)benzamide.

B) (E)-N-(4-Methyl-3-(2-(6-(pyridin-3-ylamino)-9H-purin-9-yl)vinyl)phenyl)-3-(trifluoromethyl)benzamide (E)-N-(3-(2-(6-Chloro-9H-purin-9-yl)vinyl)-4-methylphenyl)-3-(trifluoromethyl)benzamide (0.046 g, 0.10 mmol), 3-aminopyridine (0.022 g, 0.22 mmol), Pd2(dba)$_3$ (5 mol %), 2-(dicyclohexylphosphino)biphenyl (7.5 mol %) and K$_3$PO$_4$ (0.032 g, 0.15 mmol) were mixed in DME. The mixture was heated at reflux under N2 for 15 h, cooled to rt, and partitioned between aq. Na$_2$CO$_3$ and EtOAc. The aqueous layer was extracted with ethyl acetate and the combined organic layers were dried over sodium sulfate, concentrated

Example 10

(E)-9-(2-(2-Chloro-4-methylpyridin-3-yl)vinyl)-N-(4-(dimethylphosphoryl)phenyl)-9H-purin-6-amine A) 2-Chloro-3-iodo-4-methylpyridine 2-Chloro-3-amino-4-methylpyridine (2.0 g, 14.6 mmol)) in concentrated HCl (8.8 mL) was cooled to 0° C. A solution of sodium nitrite (1.03 g, 15.02 mmol) in water (17.6 mL) was added and the mix. was stirred at 0° C. for 1 h. This mixture was added dropwise to a solution of Kl (3.2 g, 18.9 mmol) in water (17.6 mL) at 0° C. The reaction mix was allowed to warm to rt. This was stirred at this temp, for 12 h. The mixture was extracted with ether (3×150 mL). The combined extracts were washed with saturated aq. sodium chloride, dried (Na$_2$SO$_4$) and concentrated in vacuo. Recrystallized from Hexane/ethyl acetate and used as such in the next step.

B) (E)-9-(2-(2-Chloro-4-methylpyridin-3-yl)vinyl)-N-(4-(dimethylphosphoryl)phenyl)-9H-purin-6-amine N-(4-(Dimethylphosphoryl)phenyl)-9-vinyl-9H-purin-6-amine (Example 3, 1 mmol), 2-chloro-3-iodo-4-methylpyridine compound (1.3 mmol), disopropylethyl amine (3 mmol), palladium acetate (0.05 mmol), tri-o-tolylphosphine (0.1 mmol) in DMF (5 mL) was thoroughly purged with argon for 10-15 min. and sealed and heated for 120° C. for 18 h. until the starting materials disappeared. The reaction mix. was passed through celite, and washed with dichloromethane containing 30% methanol. The filtrate was concentrated in vacuo. The residue was purified by Biotage-S column chromatography using 1/1 hexane ethyl acetate, ethyl acetate and 1-10% methanol containing ethyl acetate: MS [M+H]$^+$ 439.

Example 11

(E)-9-(2,6-dimethylstyryl)-N-(4-(dimethylphosphoryl)phenyl)-9H-purin-6-amine

The titled compound was made as for example 10: MS [M+H]$^+$ 418.

Example 12

(E)-9-(2-chloro-6-methylstyryl)-N-(4-(dimethylphosphoryl)phenyl)-9H-purin-6-amine The titled compound was made as for example 10: MS [M+H]$^+$ 438.

Example 13

(E)-9-(2-chloro-6-fluorostyryl)-N-(4-(dimethylphosphoryl)phenyl)-9H-purin-6-amine The titled compound was made as for example 10: MS [M+H]$^+$ 442.

Example 14

(E)-9-(2-methyl-6-ethylstyryl)-N-(4-(dimethylphosphoryl)phenyl)-9H-purin-6-amine The titled compound was made as for example 10: MS [M+H]$^+$ 432.

Example 15

(E)-9-(2-methyl-6-aminostyryl)-N-(4-(dimethylphosphoryl)phenyl)-9H-purin-6-amine The titled compound was made as for example 10: MS [M+H]$^+$ 419.

Example 16

(E)-9-(2-methyl-6-aminostyryl)-N-(4-(dimethylphosphoryl)phenyl)-9H-purin-6-amine The titled compound was made as for example 10: MS [M+H]$^+$ 419.

Example 17

(E)-9-(2-(1H-indol-4-yl)vinyl)-N-(4-(dimethylphosphoryl)phenyl)-9H-purin-6-amine The titled compound was made as for example 10: MS [M+H]$^+$ 429.

Example 18

(E)-4-(2-(6-(4-(dimethylphosphoryl)phenylamino)-9H-purin-9-yl)vinyl)indolin-2-one The titled compound was made as for example 10: MS [M+H]$^+$ 445.

Example 19

(E)-9-(2-(1H-indazol-4-yl)vinyl)-N-(4-(dimethylphosphoryl)phenyl)-9H-purin-6-amine A. tert-Butyl 4-bromo-1H-indazole-1-carboxylate To a solution of 4-bromo indazole (1.2 g, 5.6 mmol) in THF (15 mL) was added DMAP (0.068 g, 0.56 mmol) followed by BOC-anhydride (1.8 g, 8.4 mmol) and this was stirred at rt. for 5 h. THF was evaporated and the residue was extracted with dichloromethane (3×75 mL) which was washed successively with potassium hydrogen sulfate (10%) solution (10 mL×2), followed by water (10 mL), dried over sodium sulfate and concentrated in vacuo to give a gum which was purified on a Biotage-S silica gel column using hexane/ethyl acetate (80-100%) to give a colorless foam.

(continued on previous column: on a rotavap, and then purified by RP HPLC (acetonitrile/water/0.1% TFA): MS [M+H]$^+$ 515.)

B. (E)-tert-Butyl 4-(2-(6-(4-(dimethylphosphoryl) phenylamino)-9H-purin-9-yl)vinyl)-1H-indazole-1-carboxylate The title compound was made as for example 10B.

C. (E)-9-(2-(1H-indazol-4-yl)vinyl)-N-(4-(dimethylphosphoryl)phenyl)-9H-purin-6-amine

Example 20

(E)-N-(4-(dimethylphosphoryl)phenyl)-9-(2-(5-methyl-1H-indazol-4-yl)vinyl)-9H-purin-6-amine

A. 2,6-Dimethyl-3-nitrobromo Benzene

Fuming nitric acid (83.3 mL) (>90%) was added slowly to a solution of 2,6-dimethyl bromobenzene (27.9 g, 150 mmol) in acetric acid (167 mL) and cooled in an ice-bath (above f.p). The mix was allowed to come to rt and later heated at 80° C. for 2 h. (HPLC showed no SM). Reaction mixture was cooled and poured into ice-water with stirring. The resulting yellow solid was filtered, washed with ice-water and dried to give 28.7 g of an yellow solid which was used as such in the next step.

B. 2,6-Dimethyl-3-aminobromo benzene 2,6-Dimethyl-3-nitrobromo benzene (5.7 g, 0.025 mol) was dissolved in acetic acid (60 mL) and ethanol (60 mL). To this was added iron powder (5.6 g, 0.01 mol) in small portions and after the addition, it was refluxed for 2-3 h under nitrogen. An additional 2.8 g of iron powder was added and again refluxed for another 2 h. The mixture was filtered through celite and concentrated in vacuo. The residue was neutralized with sodium carbonate solution and repeatedly extracted (×3) with boiling ethyl acetate (50 mL each). Ethyl acetate was concentrated after drying over sodium sulfate to give a brown solid which was purified by chromatography on silica gel using 4% ethyl acetate in hexane to give a pale yellow solid.

C. 5-Methyl-4-bromo indazole

To 2,6-dimethyl-3-aminobromo benzene (2.4 g, 0.12 mol) and HBF4-Water (40% by wt, 35 mL, 0.27 mol) as a slurry at 0° C. was added a solution of sodium nitrite (0.91 g, 0.013 mol). in drops. The mix was stirred at 0° C. for an additional hr and the resulting solid was filtered washed with cold water and ether and dried in a desiccator for 1 h and 20 min. Potassium acetate (91.6 g, 0.17 mol) and 18-C-6 crown ether (0.11 g, 0.00042 mol) were suspended in chloroform (ethanol free) and stirred. To this was added the diazonium salt in one portion at rt. An orange suspension turning into brown resulted. After stirring at rt for 1 h the solid was filtered. The filtrate was washed with water, dried (sodium sulfate) and concentrated in vacuo gave 5d as a white solid.

D. 5-Methyl-4-bromo-N-1-tert-butoxycarbonyl indazole

To a solution of 5-methyl-4-bromo indazole (1.2 g, 5.6 mmol) in THF (15 mL) was added DMAP (0.068 g, 0.56 mmol) followed by BOC-anhydride (1.83 g, 8.37 mmol), were stirred at rt. for 5 h. THF was evaporated and the residue was extracted with dichloromethane (3×50 mL) which was washed successively with potassium hydrogen sulfate (10%) solution (10 mL×2), followed by water (10 mL), dried over sodium sulfate and concentrated to give a gum which was purified on a Biotage-S silica gel column using 80-100% hexane/ethyl acetate.

E. (E)-tert-butyl 4-(2-(6-(4-(dimethylphosphoryl) phenylamino)-9H-purin-9-yl)vinyl)-5-methyl-1H-indazole-1-carboxylate The tiled compound was made as for example 10 B.

F. (E)-N-(4-(dimethylphosphoryl)phenyl)-9-(2-(5-methyl-1H-indol-4-yl)vinyl)-9H-purin-6-amine

Example 21

(E)-N-(4-(dimethylphosphoryl)phenyl)-9-(2-(5-methyl-1H-indol-4-yl)vinyl)-9H-purin-6-amine

A. 6-Methyl-2-N,N-dimethylaminomethyl-3-nitrobromobenzene tert-Butoxybis(dimethylaminomethane (16 g, 91 mmol) was added to a solution of 2,6-dimethyl-3-nitrobromobenzene (20 g, 87 mmol) in anhydrous DMF (120 mL) at rt. The reaction mix was heated at 120-125° C. under nitrogen for 5 h until all the starting material disappeared. It was then cooled to rt, poured into water and extracted with dichloromethane (100 mL×3). The dichloromethanes were combined and dried (sodium sulfate), filtered and concentrated to obtain a brown oil which was used in the next step without further purification.

B. 5-Methyl-4-bromo indole

The crude mixture from example 21A was dissolved in acetic acid/water (250 mL, 4/1), cooled to 0° C. and treated with zinc dust (5.7 g, 87 mmol) added in small portions. After the addition, the reaction mixture was heated at 110° C. for 4 h. Zinc was removed through a pad of celite and the filtrate was extracted in dichloromethane (100 ml×3). The combined extracts were dried over sodium sulfate, concentrated and purified by column chromatography using 10% ethyl acetate/methanol.

C. (E)-N-(4-(dimethylphosphoryl)phenyl)-9-(2-(5-methyl-1H-indol-4-yl)vinyl)-9H-purin-6-amine The titled compound was made as for example 10b: MS [M+H]$^+$ 445.

Example 22

(E)-9-(2,6-dimethylstyryl)-N-(4-dipropylphosphoryl) phenyl)-2-isopropyl-9H-purin-6-amine

A) N-(4-(Dipropylphosphoryl)phenyl)-2-iodo-9-(tetrahydro-2H-pyran-2-yl)-9H-purin-6-amine Patasium tert-Butoxide (0.19 g, 1.65 mmol) was suspended in 4.5 mL anhydrous THF under nitrogen and cooled to −10° C. in an ice-salt bath. 4-(Dipropylphosphoryl)benzenamine (0.12 g, 0.55 mmol) was added to the suspension and the mixture was stirred at −10° C. for 30 min. 6-Chloro-2-iodo-9-(tetrahydro-2H-pyran-2-yl)-9H-purine (Tetrahedron 2002, 58, 7911-7923, 0.18 mg, 0.5 mmol) was then added to the reaction mixture and the content was warmed to room temperature and stirred over night. The reaction mixture was cooled to 0° C., and quenched by the addition of 0.1N HCl (~500 mL). The mixture was concentrated on a rotavapor. The residue was partitioned between ethyl acetate (10 mL)/water (4 mL), organic layer was separated and washed with 0.1N HCl (4×4 mL), saturated NaHCO$_3$ (4 mL), brine (4 mL), and dried over Na$_2$SO$_4$. The final product was obtained by flash column chromatography on silica gel (7.5% MeOH/DCM).

B) N-(4-(Dipropylphosphoryl)phenyl)-2-isopropyl-9-(tetrahydro-2H-pyran-2-yl)-9H-purin-6-amine To a oven-dried 10 mL round bottom flask was transferred under Ar 2.88 mL Rieke Zinc (0.14 g Zn, 2.2 mmol, 5 g/100 mL THF) using a 12 gauge needle. Then isopropyl iodide (200 □L, 2 mmol) was added via syringe. The solution turned warm and the content was stirred at rt for 3 h. In a separate flask (25 mL) was dissolved N-(4-(dipropylphosphoryl)phenyl)-2-iodo-9-(tetrahydro-2H-pyran-2-yl)-9H-purin-6-amine (0.28 g, 0.5 mmol) and PdCl$_2$(PPh$_3$)$_2$ (0.035 g, 0.05 mmol) in 4.0 mL dry DMF. The Zinc reagent was transferred to the reaction via a syringe. The reaction mixture was stirred at rt overnight. 20 mL EtOAc/20 mL water was added to the reaction mixture and the content was filtered through Celite, washed with 1% MeOH/EtOAc (30 mL). The organic layer was separated and washed with water, brine, and dried Na$_2$SO$_4$. The final product was purified on silica gel (4-7.5% MeOH/DCM).

C) N-(4-(Dipropylphosphoryl)phenyl)-2-isopropyl-9H-purin-6-amine

N-(4-(Dipropylphosphoryl)phenyl)-2-isopropyl-9-(tetrahydro-2H-pyran-2-yl)-9H-purin-6-amine (0.23 g) was added 50%/50% TFA/DCM (6 mL) and the resulting solution was stirred at rt for 15 min. HPLC showed the completion of the reaction. Solvent was removed on a rotavapor. The residue was dissolved in 30 mL ethyl acetate and the organic solution was washed 5% NaHCO$_3$ (10 mL), brine (10 mL) and dried over anhydrous Na$_2$SO$_4$. The final product was obtained by flash column chromatography on silica gel (10% MeOH/DCM).

D) (Dipropylphosphoryl)methyl 4-methylbenzenesulfonate

To dipropyl hydroxymethylphosphine-oxide (Ref. U.S. Pat. No. 5,272,128) (16.4 g, 0.1 mol) in anhydrous ether (200 mL) at 0° C., was added p-toluenesulfonyl chloride (19.1 g, 0.1 mol), triethyl amine (27.8 mL, 0.2 mol). The reaction was stirred at room temperature over night. The ether solution was decanted, and the precipitate was washed in a filter funnel with ~1 L ether until HPLC found no product. Combined ether layer were concentrated. The crude product was purified on silica gel chromatography with 8% MeOH/DCM.

E) 9-((Dipropylphosphoryl)methyl)-N-(4-(dipropylphosphoryl)phenyl)-2-isopropyl-9H-purin-6-amine In a 80 mL CEM microwave scaleup tube, was dissolved 1e (1.0 g, 2.6 mmol) in 20 mL anhydrous DMF. NaH (60% dispersion in mineral oil, 0.13 g, 3.12 mmol) was added portionwise. The reaction was stirred at room temperature for 20 min. Then (dipropylphosphoryl)methyl 4-methylbenzenesulfonate (0.91 g, 2.86 mmol) was added. The reaction was put on microwave (120° C./10 min). The reaction mixture was partitioned in between EtOAc/H$_2$O, organic layer was dried with Na$_2$SO$_4$. The product was purified by flash column chromatography on silica gel (10% MeOH/DCM).

F) (E or Z)-9-(2,6-dimethylstyryl)-N-(4-(dipropylphosphoryl)phenyl)-2-isopropyl-9H-purin-6-amine 9-((Dipropylphosphoryl)methyl)-N-(4-(dipropylphosphoryl)phenyl)-2-isopropyl-9H-purin-6-amine (0.15 g, 0.28 mmol) was dissolved in dry DMF (1 mL) in a 10 mL CEM microwave tube. NaH (0.033 g, 60% dispersion in mineral oil, 0.79 mmol) was added and stirred at room temperature for 10 min until no more bubbling. Then 2,6-dimethylbenaldehyde (0.10 g, 0.972 mmol) was added and the reaction was heated on microwave (120° C./20 min). The reaction was partitioned EtOAc/H$_2$O (10 ml/10 ml) and the organic layer was separated and dried (Na$_2$SO$_4$). The E-isomer (24 mg) was obtained after column chromatography on silica gel (5% MeOH/DCM), followed by Z isomer (8 mg): MS [M+H]$^+$ 516.

Example 23

(E)-N-(4-(dipropylphosphoryl)phenyl)-2-isopropyl-9-styryl-9H-purin-6-amine

The titled compound was made as for example 22: MS [M+H]$^+$ 488.

Example 24

N-(4-(Dipropylphosphoryl)phenyl)-2-isopropyl-9-(2-methylprop-1-enyl)-9H-purin-6-amine The titled compound was made as for example 22: MS [M+H]$^+$ 440.

Example 25

9-(Cyclohexylidenemethyl)-N-(4-(dipropylphosphoryl)phenyl)-2-isopropyl-9H-purin-6-amine The titled compound was made as for example 22: MS [M+H]$^+$ 480.

Example 26

(E)-9-(2-cyclopropylvinyl)-N-(4-(dipropylphosphoryl)phenyl)-2-isopropyl-9H-purin-6-amine The titled compound was made as for example 22: MS [M+H]$^+$ 452.

Example 27

(E)-9-(2,6-dimethylstyryl)-N-(4-(dimethylphosphoryl)phenyl)-2-morpholino-9H-purin-6-amine A) 2-chloro-N-(4-(dimethylphosphoryl)phenyl)-9-vinyl-9H-purin-6-amine To a sealed tube were added 2,6-dichloropurine-9-vinyl purine (0.43 g, 2 mmol), 4-aminophenyl-dimethylphosphine oxide (0.37 g, 2.2 mmol), and the solids were dissolved in ~15 mL anhydrous EtOH under Ar. Then DIEA (1.0 mL, 6 mmol) was added. The reaction was heated at 105° C. for 3 overnights until the starting material 2,6-dichloro-9-vinylpurine had disappeared. Volatiles were removed by rotavaporing and the residue was partitioned between EtOAc/water. The organic layer was washed with water once more and dried over $Na_2SO_4$. The final product was purified by silica gel column chromatography (4~8% MeOH/DCM).

B) (E)-9-(2,6-dimethylstyryl)-2-chloro-N-(4-(dimethylphosphoryl)phenyl)-9H-purin-6-amine To an oven-dried 50 mL round-bottom flask were added 2-chloro-N-(4-(dimethylphosphoryl)phenyl)-9-vinyl-9H-purin-6-amine (0.32 g, 0.93 mmol), $Pd(OAc)_2$ (10 mg, 0.05 mmol), tri-o-tolylphosphine (30 mg, 0.1 mmol), 2-iodo-m-xylene (0.39 g, 1.67 mmol). The mixture was flushed with Ar and then dissolved in ~10 mL anhydrous DMF. DIEA (0.39 g, 2.79 mmol) was then added via syringe. The reaction was stirred at 110° C. overnight. The reaction was diluted with EtOAc and filtered through celite, washed with ample ~5% MeOH/EtOAc, the combined organic layer was washed with water twice, dried over $Na_2SO_4$. Final product was purified by silica gel column chromatography (4~8% MeOH/DCM).

C) N-(4-(dimethylphosphoryl)phenyl)-2-fluoro-9-vinyl-9H-purin-6-amine

The titled compound was made as for example 27A.

D) (E)-9-(2,6-dimethylstyryl)-N-(4-(dimethylphosphoryl)phenyl)-2-fluoro-9H-purin-6-amine The titled compound was made as for example 27B E) (E)-9-(2,6-dimethylstyryl)-N-(4-(dimethylphosphoryl)phenyl)-2-morpholino-9H-purin-6-amine 2-chloro-N-(4-(dimethylphosphoryl)phenyl)-9-vinyl-9H-purin-6-amine (0.05 g, 0.11 mmol) was dissolved in n-BuOH/DMSO (1.0 mL/0.2 mL) in a CEM 10 mL microwave tube and was added morpholine (95 □L, 1.1 mmol) and DIEA (96 □L, 0.55 mmol). The reaction was heated with microwave (120° C., 10 min). Solvent was removed on a rotavapor and the residue was partitioned between EtOAc/water, organic layer was separated and dried $Na_2SO_4$. The product was purified on ISCO combiFlash (12 g silica gel column, 5% MeOH/DCM) to yield the desired compound: MS $[M+H]^+$ 559.

Example 28

(E)-9-(2,6-dimethylstyryl)-$N^6$-(4-(dimethylphosphoryl)phenyl)-9H-purine-2,6-diamine The titled compound was made as for example 27: MS $[M+H]^+$ 433

Example 29

(E)-2-(4-(9-(2,6-dimethylstyryl)-6-(4-(dimethylphosphoryl)phenylamino)-9H-purin-2-yl)piperazin-1-yl)ethanol The titled compound was made as for example 27.

Example 30

(E)-9-(2,6-dimethylstyryl)-$N^6$-(4-(dimethylphosphoryl)phenyl)-$N^2$,$N^2$-dimethyl-9H-purine-2,6-diamine The titled compound was made as for example 27.

Example 31

(E)-9-(2,6-dimethylstyryl)-N-(4-(dimethylphosphoryl)phenyl)-2-(pyrrolidin-1-yl)-9H-purin-6-amine The titled compound was made as for example 27.

Example 32

(E)-9-(2,6-dimethylstyryl)-$N^2$-(2-(dimethylamino)ethyl)-$N^6$-(4-(dimethylphosphoryl)phenyl)-9H-purine-2,6-diamine The titled compound was made as for example 27.

Example 33

(E)-9-(2,6-dimethylstyryl)-$N^2$-(2-(dimethylamino)ethyl)-$N^6$-(4-(dimethylphosphoryl)phenyl)-$N^2$-ethyl-9H-purine-2,6-diamine The titled compound was made as for example 27.

Example 34

(E)-9-(2,6-dimethylstyryl)-$N^6$-(4-(dimethylphosphoryl)phenyl)-$N^2$-(2-methoxyethyl)-9H-purine-2,6-diamine The titled compound was made as for example 27.

Example 35

(E)-9-(2,6-dimethylstyryl)-$N^2$-(4-aminocyclohexyl)-$N^6$-(4-(dimethylphosphoryl)phenyl)-9H-purine-2,6-diamine The titled compound was made as for example 27 MS $[M+H]^+$ 530.

Example 36

(E)-9-(2,6-dimethylstyryl)-N-(4-(dimethylphosphoryl)phenyl)-2-(piperazin-1-yl)-9H-purin-6-amine The titled compound was made as for example 27: MS $[M+H]^+$ 502

Example 37

(E)-9-(2,6-dimethylstyryl)-$N^2$-cyclopropyl-$N^6$-(4-(dimethylphosphoryl)phenyl)-9H-purine-2,6-diamine The titled compound was made as for example 27: MS $[M+H]^+$ 473.

Example 38

(R,E)-2-(9-(2,6-dimethylstyryl)-6-(4-(dipropylphosphoryl)phenylamino)-9H-purin-2-ylamino)-3-methylbutan-1-ol The titled compound was made as for example 27: MS [M+H]$^+$ 575

Example 39

(E)-9-(2,6-dimethylstyryl)-2-(4-(aminomethyl)piperidin-1-yl)-N-(4-(dipropylphosphoryl)phenyl)-9H-purin-6-amine The titled compound was made as for example 27: MS [M+H]$^+$ 586.

Example 40

(E)-9-(2,6-dimethylstyryl)-N-(4-(dimethylphosphoryl)phenyl)-2-(1H-imidazol-1-yl)-9H-purin-6-amine Imidazole (0.16 g, 2.36 mmol) was dissolved in DMF (1.0 mL) in a CEM 10 mL microwave tube and to this was added NaH (0.09 g, 60% dispersion in mineral oil). The content was stirred at room temperature until no more bubbling was observed (~10 min). Then (E)-9-(2,6-dimethylstyryl)-2-chloro-N-(4-(dimethylphosphoryl)phenyl)-9H-purin-6-amine (0.12 g, 0.236 mmol) was added. The reaction was heated with microwave (120° C., 10 min). Solvent was removed on rotavapor and the residue was partitioned between EtOAc/water, and the organic layer was separated and dried Na$_2$SO$_4$. The product was purified on ISCO combiFlash (12 g silica gel column, 5% MeOH/DCM): MS [M+H]$^+$ 484.

Example 41

(E)-9-(2,6-dimethylstyryl)-N-(4-(dimethylphosphoryl)phenyl)-2-(4-methyl-1H-imidazol-1-yl)-9H-purin-6-amine The titled compound was made as for example 40: MS [M+H]$^+$ 498.

Example 42

(E)-9-(2,6-dimethylstyryl)-N-(4-(dimethylphosphoryl)phenyl)-2-methoxy-9H-purin-6-amine The titled compound was made as for example 40: MS [M+H]$^+$ 448.

Example 43

(E)-9-(2,6-dimethylstyryl)-2-(2-(dimethylamino)ethoxy)-N-(4-(dipropylphosphoryl)phenyl)-9H-purin-6-amine The titled compound was made as for example 40: MS [M+H]$^+$ 505.

Example 44

(E)-9-(2,6-dimethylstyryl)-N-(4-(dimethylphosphoryl)phenyl)-2-(2-methoxyethoxy)-9H-purin-6-amine The titled compound was made as for example 40: MS [M+H]$^+$ 498.

Example 45

(E)-9-(2,6-dimethylstyryl)-N-(4-(dimethylphosphoryl)phenyl)-2-(tetrahydro-2H-pyran-4-yloxy)-9H-purin-6-amine The titled compound was made as for example 40: MS [M+H]$^+$ 518.

Example 46

(E)-9-(2,6-dimethylstyryl)-N-(4-(dimethylphosphoryl)phenyl)-2-(tetrahydrofuran-3-yloxy)-9H-purin-6-amine The titled compound was made as for example 40: MS [M+H]$^+$ 504.

Example 47

(E)-9-(2,6-dimethylstyryl)-2-(cyclopentyloxy)-N-(4-(dimethylphosphoryl)phenyl)-9H-purin-6-amine The titled compound was made as for example 40.

Example 48

(E)-9-(2,6-dimethylstyryl)-N-(4-(dimethylphosphoryl)phenyl)-2-(1-methylpiperidin-4-yloxy)-9H-purin-6-amine The titled compound was made as for example 40: MS [M+H]$^+$ 531.

Example 49

(E)-9-(2,6-dimethylstyryl)-N-(4-(dimethylphosphoryl)phenyl)-2-(pyridin-3-yloxy)-9H-purin-6-amine The titled compound was made as for example 40: MS [M+H]$^+$ 511.

Example 50

(E)-9-(2,6-dimethylstyryl)-N-(4-(dimethylphosphoryl)phenyl)-2-(methylthio)-9H-purin-6-amine (E)-9-(2,6-Dimethylstyryl)-2-chloro-N-(4-(dimethylphosphoryl)phenyl)-9H-purin-6-amine (0.20 g, 0.442 mmol) was dissolved in 2 mL dry DMF together with NaSMe (0.31 g, 4.42 mmol) in a 10 mL CEM microwave tube. The content was heated on microwave (120° C./10 min). The reaction was worked up as usual and product was purified with ISCO combiFlash (12 gram SiO$_2$ column, 5% MeOH/DCM): MS [M+H]$^+$ 464.

Example 51

(E)-9-(2,6-dimethylstyryl)-N-(4-(dimethylphosphoryl)phenyl)-2-(methylsulfonyl)-9H-purin-6-amine (E)-9-(2,6-Dimethylstyryl)-N-(4-(dimethylphosphoryl)phenyl)-2-(methylthio)-9H-purin-6-amine (0.11 g, 0.226 mmol) was dissolved in 1 mL DCM in a CEM 10 mL microwave tube and was added MCPBA (0.11 g, 72% purity, 0.452 mmol). The reaction was heated on microwave (60° C./5 min). Solvent was removed and the product was purified on ISCO combiFlash (12 g SiO$_2$ column, 7% MeOH/DCM): MS [M+H]$^+$ 496.

Example 52

(E)-9-(2,6-dimethylstyryl)-2-isopropyl-N-(4-(dimethylphosphoryl)phenyl)-9H-purin-6-amine

A) 6-chloro-2-iodo-9-vinyl-9H-purine

In a 250 mL pressure tube, Hg(OAc)$_2$ (2.52 g, 7.88 mmol) was suspended in vinyl acetate (73 mL, 788 mmol). To this suspension was added H$_2$SO$_4$/EtOAc (1.5 mL/15 mL). A clear solution was formed. The 2-iodo-6-chloro-9H-purine (22.1 g, 78.8 mmol) was added. A suspension formed again. It was degassed and stirred at 45-50° C. overnight. A dark solution was formed. The mixture was passed through celite, washed with EtOAc. Organic layer was washed with Sat. NaHCO$_3$> dried Na$_2$SO$_4$. The product was purified on silica gel chromatography column (1-5% MeOH/DCM).

B) N-(4-(Dimethylphosphoryl)phenyl)-2-iodo-9-vinyl-9H-purin-6-amine

The titled compounds was made as for 22A.

C) N-(4-(Dimethylphosphoryl)phenyl)-2-isopropyl-9-vinyl-9H-purin-6-amine

In a dry Argon atmosphere Reike Zinc/THF suspension (5 g/100 mL) (2.54 mL, 2.0 mmol) was transferred into a round-bottom flask via syringe with a 12 gauge needle. Then isopropyl iodide (0.18 mL, 1.82 mmol) was added and stirring was started right away. The content turned warm and stirring was continued at rt for 4-5 hours. In a 10 mL CEM microwave tube was dissolved N-(4-(dimethylphosphoryl)phenyl)-2-iodo-9-vinyl-9H-purin-6-amine (0.20 g, 0.46 mmol), PdCl$_2$(PPh$_3$)$_2$ (19 mg, 0.027 mmol) in 1 mL dry DMF. Isopropylzinc iodide/THF solution was transferred to the microwave tube via syringe. The reaction was heated on microwave (60° C./5 min). The reaction mixture was filtered through celite, washed with EtOAc, the filtrate was concentrated, purified on ISCO combiFlash Column (SiO$_2$, 12 g).

D) (E)-9-(2,6-dimethylstyryl)-2-isopropyl-yl-(4-(dimethylphosphoryl)phenyl)-9H-purin-6-amine The titled compound was made as for 27B: MS [M+H]$^+$ 460.

Example 53

(E)-9-(2,6-dimethylstyryl)-2-sec-butyl-N-(4-(dimethylphosphoryl)phenyl)-9H-purin-6-amine The titled compound was made as for example 52: MS [M+H]$^+$ 474.

Example 54

(E)-9-(2,6-dimethylstyryl)-2-cyclohexyl-N-(4-(dimethylphosphoryl)phenyl)-9H-purin-6-amine The titled compound was made as for example 52: MS [M+H]$^+$ 500.

Example 55

(E)-9-(2,6-dimethylstyryl)-2-cyclopentyl-N-(4-(dimethylphosphoryl)phenyl)-9H-purin-6-amine The titled compound was made as for example 52: MS [M+H]$^+$ 486.

Example 56

(E)-9-(2,6-dimethylstyryl)-N-(4-(dimethylphosphoryl)phenyl)-2-isobutyl-9H-purin-6-amine The titled compound was made as for example 52: MS [M+H]$^+$ 474.

Example 57

(E)-9-(2,6-dimethylstyryl)-N-(4-(dimethylphosphoryl)phenyl)-2-(pentan-3-yl)-9H-purin-6-amine The titled compound was made as for example 52: MS [M+H]$^+$ 488.

Example 58

(E)-3-(9-(2,6-dimethylstyryl)-6-(4-(dimethylphosphoryl)phenylamino)-9H-purin-2-yl)propanenitrile The titled compound was made as for example 52: MS [M+H]$^+$ 471.

Example 59

(E)-9-(2,6-dimethylstyryl)-2-(5-chlorothiophen-2-yl)-N-(4-(dimethylphosphoryl)phenyl)-9H-purin-6-amine The titled compound was made as for example 52: MS [M+H]$^+$ 535.

Example 60

(E)-9-(2,6-dimethylstyryl)-N-(4-(dimethylphosphoryl)phenyl)-2-(thiophen-2-yl)-9H-purin-6-amine The titled compound was made as for example 52: MS [M+H]$^+$ 500.

Example 61

(E)-9-(2,6-dimethylstyryl)-N-(4-(dimethylphosphoryl)phenyl)-2-(5-methylpyridin-2-yl)-9H-purin-6-amine The titled compound was made as for example 52: MS [M+H]+ 509.

Example 62

(E)-9-(2,6-dimethylstyryl)-N-(4-(dimethylphosphoryl)phenyl)-2-(4-methylpyridin-2-yl)-9H-purin-6-amine The titled compound was made as for example 52: MS [M+H]+ 509.

Example 63

(E)-N-(4-methyl-3-(2-(6-(2-N,N-dimethylaminoethylamino)-9H-purin-9-yl)vinyl)phenyl)-3-(trifluoromethyl)benzamide The titled compound was made as for example 1 using N-(2-N,N-dimethylaminoethyl)-9-vinyl-9H-purin-6-amine: MS [M+H]+ 510.

Example 64

(E)-N-(4-methyl-3-(2-(6-(cyclopropylamino)-9H-purin-9-yl)vinyl)phenyl-3-(trifluoromethyl)benzamide The titled compound was made as for example 1 using N-Cyclopropyl-9-vinyl-9H-purin-6-amine: MS [M+H]+ 479.

Example 65

(E)-3-(2-(6-(Phenylamino)-9H-purin-9-yl)vinyl)-4-methyl-N-(3-(4-methyl-1-imidazol-1-yl)-5-(trifluoromethyl)phenyl)benzamide The titled compound was made as for example 4 using N-phenyl-9-vinyl-9H-purin-6-amine: MS [M+H]+ 595.

Example 66

(E)-N-(4-Methyl-3-(2-(6-(pyridin-4-ylamino)-9H-purin-9-yl)vinyl)phenyl)-3-(trifluoromethyl)benzamide The titled compound was made as for example 9 using 4-aminopyridine: MS [M+H]+ 515.

Example 67

(E)-N-(4-Methyl-3-(2-(6-(pyridin-2-ylamino)-9H-purin-9-yl)vinyl)phenyl)-3-(trifluoromethyl)benzamide The titled compound was made as for example 9 using 2-aminopyridine: MS [M+H]+ 515.

Example 68

(E)-N-(4-methyl-3-(2-(6-(3-N,N-dimethylaminopropylamino)-9H-purin-9-yl)vinyl)phenyl)-3-(trifluoromethyl)benzamide The titled compound was made as for example 1 using N-(3-N,N-dimethylaminopropyl)-9-vinyl-9H-purin-6-amine: MS [M+H]+ 524.

Example 69

(E)-3-(2-(6-(4-(Dimethylphosphoryl)phenylamino)-9H-purin-9-yl)vinyl)-4-methyl-N-(3-(trifluoromethyl)phenyl)benzamide The titled compound was made as for example 4 using 3-iodo-4-methyl-N-(3-(trifluoromethyl)phenyl)benzamide and N-(4-(dimethylphosphoryl)phenyl)-9-vinyl-9H-purin-6-amine: MS [M+H]+ 591.

Example 70

(E)-3-(2-(6-(4-(Dimethylphosphoryl)phenylamino)-9H-purin-9-yl)vinyl)-4-methyl-N-(5-tert-butylisoxazol-3-yl)benzamide The titled compound was made as for example 4 using 3-iodo-4-methyl-N-(5-tert-butylisoxazol-3-yl)benzamide and N-(4-(dimethylphosphoryl)phenyl)-9-vinyl-9H-purin-6-amine: MS [M+H]+ 570.

Example 71

(E)-N-(4-Methyl-3-(2-(6-(pyrimidin-4-ylamino)-9H-purin-9-yl)vinyl)phenyl)-3-(trifluoromethyl)benzamide The titled compound was made as for example 9 using 4-aminopyrimidine: MS [M+H]+ 517.

Example 72

(E)-N-(4-methyl-3-(2-(6-(1-methylpiperidin-4-ylamino)-9H-purin-9-yl)vinyl)phenyl-3-(trifluoromethyl)benzamide The titled compound was made as for example 1 using 1-methylpiperidin-4-amine: MS [M+H]+ 536.

Example 73

(E)-3-(2-(6-Cyclopropylamino)-9H-purin-9-yl)vinyl)-4-methyl-N-(5-tert-butylisoxazol-3-yl)benzamide The titled compound was made as for example 4 using 3-iodo-4-methyl-N-(5-tert-butylisoxazol-3-yl)benzamide and N-cyclopropyl-9-vinyl-9H-purin-6-amine: MS [M+H]+ 458.

Example 74

(E)-3-(2-(6-Cyclopropylamino)-9H-purin-9-yl)vinyl)-4-methyl-N-(3-tert-butyl-1-methylpyrazol-5-yl)benzamide The titled compound was made as for example 4 using 3-iodo-4-methyl-N-(3-tert-butyl-1-methylpyrazol-5-yl)benzamide and N-cyclopropyl-9-vinyl-9H-purin-6-amine: MS [M+H]$^+$ 471.

Example 75

(E)-3-(2-(6-Cyclopropylamino)-9H-purin-9-yl)vinyl)-4-methyl-N-(3-tert-butylpyrazol-5-yl)benzamide The titled compound was made as for example 4 using 3-iodo-4-methyl-N-(3-tert-butylpyrazol-5-yl)benzamide and N-cyclopropyl-9-vinyl-9H-purin-6-amine: MS [M+H]$^+$ 457.

Example 76

(E)-3-(2-(6-Cyclopropylamino)-9H-purin-9-yl)vinyl)-4-methyl-N-(3-tert-butylphenyl)benzamide The titled compound was made as for example 4 using 3-iodo-4-methyl-N-(3-tert-butylphenyl)benzamide and N-cyclopropyl-9-vinyl-9H-purin-6-amine: MS [M+H]$^+$ 467.

Example 77

(E)-3-(2-(6-Cyclopropylamino)-9H-purin-9-yl)vinyl)-4-methyl-N-(4-chloro-3-trifluoromethylphenyl)benzamide The titled compound was made as for example 4 using 3-iodo-4-methyl-N-(4-chloro-3-trifluoromethylphenyl)benzamide and N-cyclopropyl-9-vinyl-9H-purin-6-amine: MS [M+H]$^+$ 514.

Example 78

(E)-3-(2-(6-Cyclopropylamino)-9H-purin-9-yl)vinyl)-4-methyl-N-(2-fluoro-5-trifluoromethylphenyl)benzamide The titled compound was made as for example 4 using 3-iodo-4-methyl-N-(2-fluoro-5-trifluoromethylphenyl)benzamide and N-cyclopropyl-9-vinyl-9H-purin-6-amine: MS [M+H]$^+$ 497.

Example 79

(E)-3-(2-(6-Amino-9H-purin-9-yl)vinyl)-4-methyl-N-(4-(trifluoromethyl)pyridin-2-yl)benzamide The titled compound was made as for example 4 using 3-iodo-4-methyl-N-(4-(trifluoromethyl)pyridin-2-yl)benzamide and 9-vinyl-9H-purin-6-amine: MS [M+H]$^+$ 440.

Example 80

(E)-N-(3-(2-(6-(4-(Dimethylphosphoryl)phenylamino)-9H-purin-9-yl)vinyl)-4-methylphenyl)nicotinamide The titled compound was made as for example 1 using N-(4-(dimethylphosphoryl)phenyl)-9-vinyl-9H-purin-6-amine and N-(3-iodo-4-methylphenyl)nicotinamide: MS [M+H]$^+$ 524.

Example 81

(E)-N-(3-(2-(6-(4-(Dimethylphosphoryl)phenylamino)-9H-purin-9-yl)vinyl)-4-methylphenyl)-5-cyclopropylisoxazole-3-carboxamide The titled compound was made as for example 1 using N-(4-(dimethylphosphoryl)phenyl)-9-vinyl-9H-purin-6-amine and N-(3-iodo-4-methylphenyl)-5-cyclopropyl-3-carboxamide: MS [M+H]$^+$ 554.

Example 82

(E)-N-(3-(2-(6-(4-cyanophenylamino)-9H-purin-9-yl)vinyl)-4-methylphenyl)-3-(trifluoromethyl)benzamide The titled compound was made as for example 9 using 4-aminobenzonitrile: MS [M+H]$^+$ 540.

Example 83

(E)-3-(2-(6-(Cyclopropylamino)-9H-purin-9-yl)vinyl)-4-methyl-N-(3-isopropylphenyl)benzamide The titled compound was made as for example 4 using 3-iodo-4-methyl-N-(3-isopropylphenyl)benzamide and N-cyclopropyl-9-vinyl-9H-purin-6-amine: MS [M+H]$^+$ 453.

Example 84

(E)-3-(2-(6-(Cyclopropylamino)-9H-purin-9-yl)vinyl)-4-methyl-N-(4-methylpyridin-2-yl)benzamide The titled compound was made as for example 4 using 3-iodo-4-methyl-N-(4-methylpyridin-2-yl)benzamide and N-cyclopropyl-9-vinyl-9H-purin-6-amine: MS [M+H]$^+$ 426.

Example 85

Biological Evaluation of Compounds

Compounds of this invention may be evaluated in a variety of assays to determine their biological activities. For example, the compounds of the invention can be tested for their ability to inhibit various protein kinases of interest. The compounds can also be evaluated for their cytotoxic and growth inhibitory effects on tumor cells of interest. See e.g., WO 03/000188, pages 115-136, the full contents of which are incorporated herein by reference.

Kinase Inhibition

More specifically, the compounds described herein are screened for kinase inhibition activity as follows. Kinases suitable for use in the following protocol include, but are not limited to: Abl, Lck, Lyn, Src, Fyn, Syk, Zap-70, Itk, Tec, Btk, EGFR, ErbB2, Kdr, Flt1, Flt-3, Tek, c-Met, InsR, and AKT.

Kinases are expressed as either kinase domains or full length constructs fused to glutathione S-transferase (GST) or polyHistidine tagged fusion proteins in either *E. coli* or Baculovirus-High Five expression systems. They are purified to near homogeneity by affinity chromatography as previously described (Lehr et al., 1996; Gish et al., 1995). In some instances, kinases are co-expressed or mixed with purified or partially purified regulatory polypeptides prior to measurement of activity.

Kinase activity and inhibition are measured by established protocols (see e.g., Braunwalder et al., 1996). Briefly, the transfer of $^{33}PO_4$ from ATP to the synthetic substrates poly (Glu, Tyr) 4:1 or poly(Arg, Ser) 3:1 attached to the bioactive surface of microtiter plates is taken as a measure of enzyme activity. After an incubation period, the amount of phosphate transferred is measured by first washing the plate with 0.5% phosphoric acid, adding liquid scintillant, and then counting in a liquid scintillation detector. The IC50 is determined by the concentration of compound that causes a 50% reduction in the amount of $^{33}P$ incorporated onto the substrate bound to the plate.

Other methods relying upon the transfer of phosphate to peptide or polypeptide substrate containing tyrosine, serine, threonine or histidine, alone, in combination with each other, or in combination with other amino acids, in solution or immobilized (i.e., solid phase) are also useful.

For example, transfer of phosphate to a peptide or polypeptide can also be detected using scintillation proximity, Fluorescence Polarization and homogeneous time-resolved fluorescence. Alternatively, kinase activity can be measured using antibody-based methods in which an antibody or polypeptide is used as a reagent to detect phosphorylated target polypeptide.

For additional background information on such assay methodologies, see e.g., Braunwalder et al., 1996, Anal. Biochem. 234(1):23; Cleaveland et al., 1990, Anal Biochem. 190(2):249 Gish et al. (1995). Protein Eng. 8(6):609 Kolb et al. (1998). Drug Discov. Toda V. 3:333 Lehr et al. (1996). Gene 169(2):27527-87 Seethala et al. (1998). Anal Biochem. 255(2):257 Wu et al. (2000).

IC50 values in the single digit nanomolar and subnanomolar (i.e., less than 1 nM) range have been observed for compounds of this invention against Src kinase.

Cell-Based Assays

Certain compounds of this invention have also been demonstrated cytotoxic or growth inhibitory effects on tumor and other cancer cell lines and thus may be useful in the treatment of cancer and other cell proliferative diseases. Compounds are assayed for anti-tumor activity using in vivo and in vitro assays which are well known to those skilled in the art. Generally, initial screens of compounds to identify candidate anti-cancer drugs are performed in cellular assays. Compounds identified as having anti-proliferative activity in such cell-based assays can then be subsequently assayed in whole organisms for anti-tumor activity and toxicity. Generally speaking, cell-based screens can be performed more rapidly and cost-effectively relative to assays that use whole organisms. For purposes of this invention, the terms "anti-tumor" and "anti-cancer" activity are used interchangeably.

Cell-based methods for measuring antiproliferative activity are well known and can be used for comparative characterization of compounds of this invention. In general, cell proliferation and cell viability assays are designed to provide a detectable signal when cells are metabolically active. Compounds may be tested for antiproliferative activity by measuring any observed decrease in metabolic activity of the cells after exposure of the cells to compound. Commonly used methods include, for example, measurement of membrane integrity (as a measure of cell viability) (e.g. using trypan blue exclusion) or measurement of DNA synthesis (e.g. by measuring incorporation of BrdU or 3H-thymidine).

Some methods for assaying cell proliferation use a reagent that is converted into a detectable compound during cell proliferation. Particularly preferred compounds are tetrazolium salts and include without limitation MTT (3-(4,5-dimethylthiazol-2-yl)-2,5-diphenyltetrazolium bromide; Sigma-Aldrich, St. Louis, Mo.), MTS (3-(4,5-dimethylthiazol-2-yl)-5-(3-carboxymethoxyphenyl)-2-(4-sulfophenyl)-2H-tetrazolium), XTT (2,3-bis(2-Methoxy-4-nitro-5-sulfophenyl)-2H-tetrazolium-5-carboxanilide), INT, NBT, and NTV (Bernas et al. Biochim Biophys Acta 1451(1):73-81, 1999). Preferred assays utilizing tetrazolium salts detect cell proliferation by detecting the product of the enzymatic conversion of the tetrazolium salts into blue formazan derivatives, which are readily detected by spectroscopic methods (Mosman. J. Immunol. Methods. 65:55-63, 1983).

Generally, preferred methods for assaying cell proliferation involve incubating cells in a desired growth medium with and without the compounds to be tested. Growth conditions for various prokaryotic and eukaryotic cells are well-known to those of ordinary skill in the art (Ausubel et al. Current Protocols in Molecular Biology. Wiley and Sons. 1999; Bonifacino et al. Current Protocols in Cell Biology. Wiley and Sons. 1999 both incorporated herein by reference). To detect cell proliferation, the tetrazolium salts are added to the incubated cultured cells to allow enzymatic conversion to the detectable product by active cells. Cells are processed, and the optical density of the cells is determined to measure the amount of formazan derivatives. Furthermore, commercially available kits, including reagents and protocols, are available for examples, from Promega Corporation (Madison, Wis.), Sigma-Aldrich (St. Louis, Mo.), and Trevigen (Gaithersburg, Md.).

A wide variety of cell types may be used to screen compounds for antiproliferative activity, including the following cell lines, among others: COLO 205 (colon cancer), DLD-1 (colon cancer), HCT-15 (colon cancer), HT29 (colon cancer), HEP G2 (Hepatoma), K-562 (Leukemia), A549 (Lung), NCI-H249 (Lung), MCF7 (Mammary), MDA-MB-231 (Mammary), SAOS-2 (Osteosarcoma), OVCAR-3 (Ovarian), PANC-1 (Pancreas), DU-145 (Prostate), PC-3 (Prostate), ACHN (Renal), CAKI-1 (Renal), MG-63 (Sarcoma).

While the cell line is preferably mammalian, lower order eukaryotic cells such as yeast may also be used to screen compounds. Preferred mammalian cell lines are derived from humans, rats, mice, rabbits, monkeys, hamsters, and guinea pigs since cells lines from these organisms are well-studied and characterized. However, others may be used as well.

Suitable mammalian cell lines are often derived from tumors. For example, the following tumor cell-types may be sources of cells for culturing cells: melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Non-limiting examples of mammalian cells lines that have been widely used by researchers include HeLa, NIH/3T3, HT1080, CHO, COS-1, 293T, WI-38 and CV1/EBNA-1.

Other cellular assays may be used which rely upon a reporter gene to detect metabolically active cells. Non-limiting examples of reporter gene expression systems include green fluorescent protein (GFP), and luciferase. As an example of the use of GFP to screen for potential antitumor drugs, Sandman et al. (Chem Biol. 6:541-51; incorporated herein by reference) used HeLa cells containing an inducible variant of GFP to detect compounds that inhibited expression of the GFP, and thus inhibited cell proliferation.

Compounds identified by such cellular assays as having anti-cell proliferation activity are then tested for anti-tumor activity in whole organisms. Preferably, the organisms are mammalian. Well-characterized mammalians systems for studying cancer include rodents such as rats and mice. Typically, a tumor of interest is transplanted into a mouse having a reduced ability to mount an immune response to the tumor to reduce the likelihood of rejection. Such mice include for example, nude mice (athymic) and SCID (severe combined immunodeficiency) mice. Other transgenic mice such as oncogene containing mice may be used in the present assays (see for example U.S. Pat. No. 4,736,866 and U.S. Pat. No. 5,175,383). For a review and discussion on the use of rodent models for antitumor drug testing see Kerbel (Cancer Metastasis Rev. 17:301-304, 1998-99).

In general, the tumors of interest are implanted in a test organism preferably subcutaneously. The organism containing the tumor is treated with doses of candidate anti-tumor compounds. The size of the tumor is periodically measured to determine the effects of the test compound on the tumor. Some tumor types are implanted at sites other than subcutaneous sites (e.g. intraperitoneal sites) and survival is measured as the endpoint. Parameters to be assayed with routine screening include different tumor models, various tumor and drug routes, and dose amounts and schedule. For a review of the use of mice in detecting antitumor compounds see Corbett et al. (Invest New Drugs. 15:207-218, 1997; incorporated herein by reference).

Example 86

Pharmaceutical Compositions

Representative pharmaceutical dosage forms of the compounds of this invention (the active ingredient being referred to as "Compound"), are provided for therapeutic or prophylactic use in humans:

| (a) Tablet I | mg/tablet |
|---|---|
| Compound | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound | 1.0 |
| Lactose Ph. Eur | 93.25 |
| Croscarmellose sodium | 4.0 |
| Maize starch paste (5% w/v paste) | 0.75 |
| Magnesium stearate | 1.0-76 |

| (d) Capsule | mg/capsule |
|---|---|
| Compound | 10 |
| Lactose Ph. Eur | 488.5 |
| Magnesium | 1.5 |

| (e) Injection I | (50 mg/ml) |
|---|---|
| Compound | 5.0% w/v |
| 1M Sodium hydroxide solution | 15.0% w/v |
| 0.1M Hydrochloric acid (to adjust pH to 7.6) | |
| Polyethylene glycol 400 | 4.5% w/v |
| Water for injection to 100% | |

| (f) Injection II | (10 mg/ml) |
|---|---|
| Compound | 1.0% W/v |
| Sodium phosphate BP | 3.6% w/v |
| 0.1M Sodium hydroxide solution | 15.0% w/v |
| Water for injection to 100% | |

| (g) Injection III | (1 mg/ml, buffered to pH 6) |
|---|---|
| Compound | 0.1% w/v |
| Sodium phosphate BP | 2.26% w/v |
| Citric acid | 0.38% w/v |
| Polyethylene glycol 400 | 3.5% w/v |
| Water for injection to 100% | |

| (h) Aerosol | 1 mg/ml |
|---|---|
| Compound | 10.0 |
| Sorbitan trioleate | 13.5 |
| Trichlorofluoromethane | 910.0 |
| Dichlorodifluoromethane | 490.0 |

| (i) Aerosol II | mg/ml |
|---|---|
| Compound | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| (j) Aerosol III | mg/ml |
|---|---|
| Compound | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

| (k) Aerosol IV | mg/ml |
|---|---|
| Compound | 2.5 |
| Soya lecithin | 2.7 |
| Trichlorofluoromethane | 67.5 |
| Dichlorodifluoromethane | 1086.0 |
| Dichlorotetrafluoroethane | 191.6 |

| (l) Ointment | ml |
|---|---|
| Compound | 40 mg |
| Ethanol | 300 μl |
| Water | 300 μl |
| 1-Dodecylazacycloheptan one | 50 μl |
| Propylene glycol | to 1 ml |

Note: These formulations may be prepared using conventional procedures well known in the pharmaceutical art. The tablets (a)-(c) may be enteric coated by conventional means, if desired to provide a coating of cellulose acetate phthalate, for example. The aerosol formulations (h)-(k) may be used in conjunction with standard, metered dose aerosol dispensers, and the suspending agents sorbitan trioleate and soya lecithin

The invention claimed is:

1. A compound of the formula:

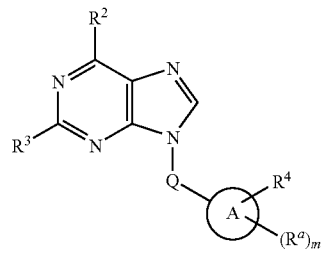

in which:
each occurrence of R² is halogen, R, —OR, —SR, —NR⁶R⁷, —CONR⁶R⁷ or —NRCO(VR), where V is —O—, —S—, —NR—, or a covalent bond;
each occurrence of R³ is -M_kR^C, where each M is independently a substituted or unsubstituted methylene moiety; k is an integer from 0 through 4; R^C is a halogen, —CN, R, —OR, —S(O)_nR, —S(O)_nNRR', —NRR', —NR(CO)VR, —CO(VR) or J, n is 0, 1 or 2;
each occurrence of R⁴ is R, —CONR⁶R⁷, —NHCOR⁶, —NHCO(OR⁶) or —NHCONR⁶R⁷;
each occurrence of R⁶ and R⁷ is independently H or an aliphatic, heteroaliphatic, aryl or heteroaryl group, or NR⁶R⁷ constitutes a N-containing heterocyclic or heteroaryl ring or ring system;
Q is —C≡C— or —CR=CR'— wherein the double bond is in either a cis- or trans-orientation;
Ring A is an aryl, heteroaryl or heterocyclic ring system;
(R^a)_m represents one or more optional substituents, R^{a1}, R^{a2}, R^{a3}, R^{a4}, R^{a5} which are selected from the group consisting of halogen, —CN, —R, —OR, —SR, —S(O)_nR, —SO_nNRR', —NRR', —(CO)VR, —O(CO)VR, —NR(CO)VR, —S(CO)VR, or —VJ, —V—C(=NR)NR'R", —COCOR, —COM_kCOR, —V—P(=O)(V'R)(V"R'), —NO₂, —NRSO₂R' and —NRSO₂NR'R" wherein V, V' and V" are independently —O—, —S—, —NR—, or a covalent bond; n is 0, 1 or 2; and m is an integer from 0 to 5;
each occurrence of R, R', R" are independently hydrogen or an aliphatic, heteroaliphatic, aryl or heteroaryl moiety; and
J is a P-containing moiety of the formula —PO(VR)₂, —P(VR)₂ or —PO(VR)(GR¹) wherein G is O, S, NR or (M)_x, and each occurrence of M is independently a substituted or unsubstituted methylene moiety; x is an integer from 1 through 6; and R¹ is —PO(VR)₂, —SO₂(VR) or —C(O)(VR); so long as any R group linked directly to P is not H;
wherein in each of the foregoing groups, each aliphatic or heteroaliphatic moiety may be branched or unbranched, cyclic or acyclic, may contain one or more unsaturated bonds and may be unsubstituted or substituted with a group selected from halogen, —CN, —R, —OR, —SR, —S(O)_nR, —SO_nNRR', —NRR', —(CO)VR, —O(CO)VR, —NR(CO)VR, —S(CO)VR, or —VJ, —V—C(=NR)NR'R", —COCOR, —COM_kCOR, —V—P(=O)(V'R) (V"R'), —NO₂, —NRSO₂R' and —NRSO₂NR'R", =O, =S, =NR, =NNRR', =NNHC(O)R, =NNHCO₂R, and =NNHSO₂R and each heterocyclic group is a non-aromatic ring system having 5-14 ring atoms of which up to four ring atoms are N, O, or S instead of C, and each heteroaryl group is a corresponding aromatic ring system;
wherein in each of the foregoing groups, each aryl, heteroaryl and heterocyclic moiety may be covalently linked to an adjacent moiety via a carbon or via a heteroatom of the heterocyclic or heteroaryl ring and may be unsubstituted or substituted with a group selected from halogen, —CN, —R, —OR, —SR, —S(O)_nR, —SO_nNRR', —NRR', —(CO)VR, —O(CO)VR, —NR(CO)VR, —S(CO)VR, or —VJ, —V—C(=NR)NR'R", —COCOR, —COM_kCOR, —V—P(=O)(V'R)(V"R'), —NO₂, —NRSO₂R' and —NRSO₂NR'R".

2. The compound of claim 1 wherein R⁴ is H.

3. The compound of claim 2 wherein

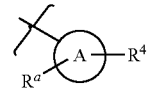

is one of the following structures:

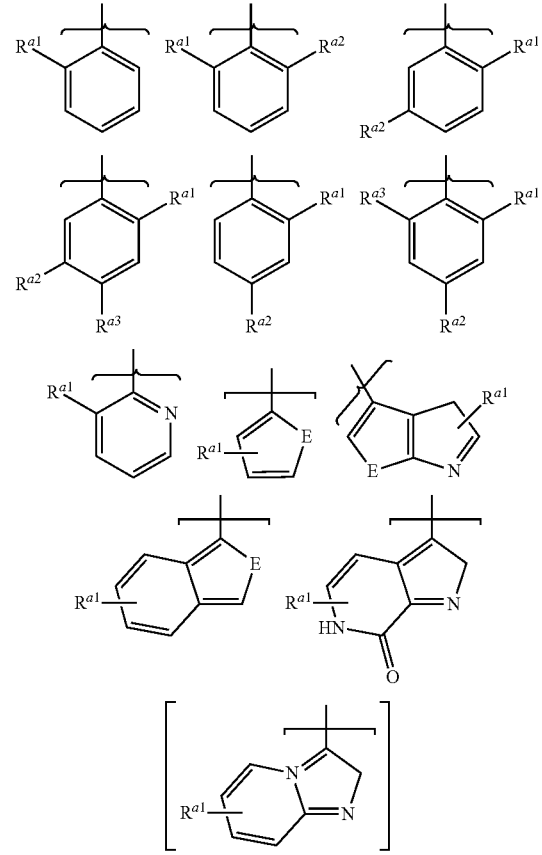

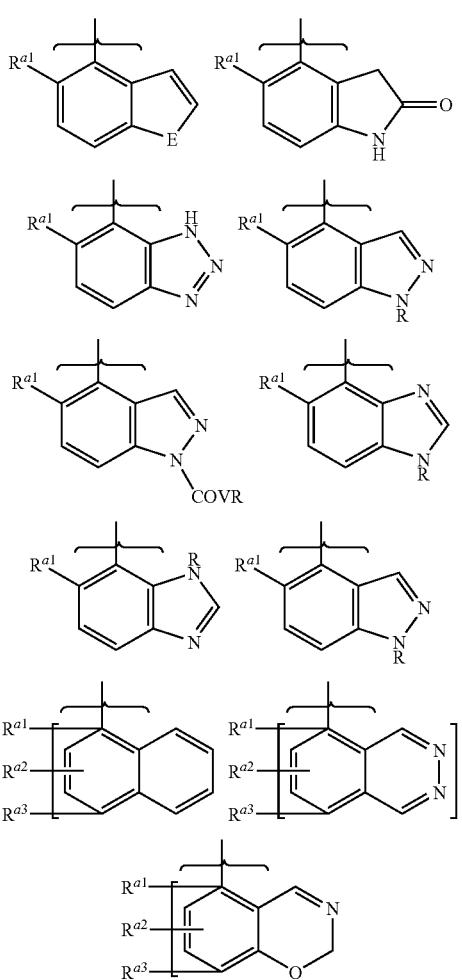

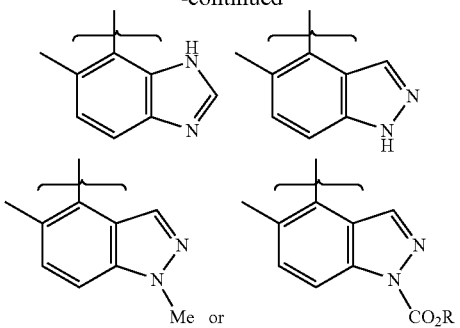

wherein E is O, S or NR and R is a hydrogen, an aliphatic, a heteroaliphatic, aryl or heteroaryl moiety.

4. The compound of claim 2 wherein

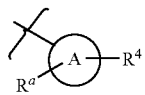

is one of the following structures:

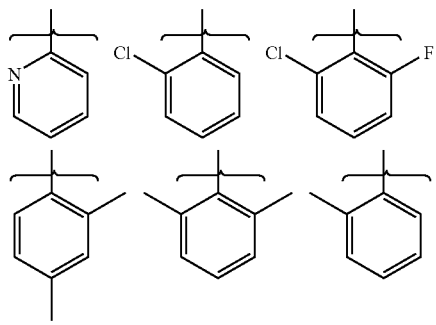

wherein R is a hydrogen, an aliphatic, a heteroaliphatic, an aryl or a heteroaryl moiety.

5. The compound of claim 1 wherein $R^4$ is —CONR$^6$R$^7$, —NHCOR$^6$ or —NHCONR$^6$R$^7$.

6. The compound of claim 5 in which $R^7$ is H.

7. The compound of claim 5 in which $R^6$ is a ring B selected from an aryl, heteroaryl or heterocyclic moiety, wherein the aryl, heteroaryl or heterocyclic moiety may contain one or more substituents selected from halo, aliphatic, heteroaliphatic, aryl or heteroaryl moiety.

8. The compound of claim 7 having the formula:

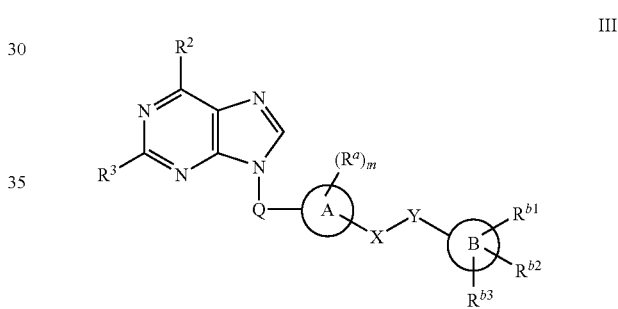

wherein Rings A and B are independently selected from an aryl, a heteroaryl and a heterocyclic rings;
—X—Y— is —CONR$^7$—, —NHCO—, or —NH-CONR$^7$—; and R$^{b1}$, R$^{b2}$ and R$^{b3}$ are selected from the group consisting of halogen, —CN, —R, —OR, —SR, —S(O)$_n$R, —SO$_n$NRR', —NRR', —(CO)VR, —O(CO)VR, —NR(CO)VR, —S(CO)VR, or —VJ, —V—C(=NR)NR'R'', —COCOR, —COM$_k$COR, —V—P(=O)(V'R)(V''R'), —NO$_2$, —NRSO$_2$R' and —NRSO$_2$NR'R'' wherein V, V' and V'' are independently —O—, —S—, —NR—, or a covalent bond; M is a substituted or unsubstituted methylene moiety; k is an integer from 0 to 4; n is 0, 1 or 2; m is an integer from 0 to 5; and R is a hydrogen, an aliphatic, a heteroaliphatic, an aryl or a heteroaryl.

9. The compound of claim 8 in which the moiety:

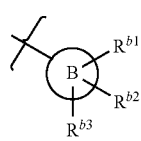

represents one of the following structures:
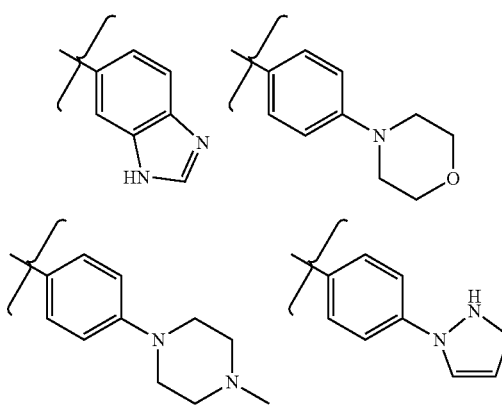
10. A compound of claim 8 having one of the following structures:
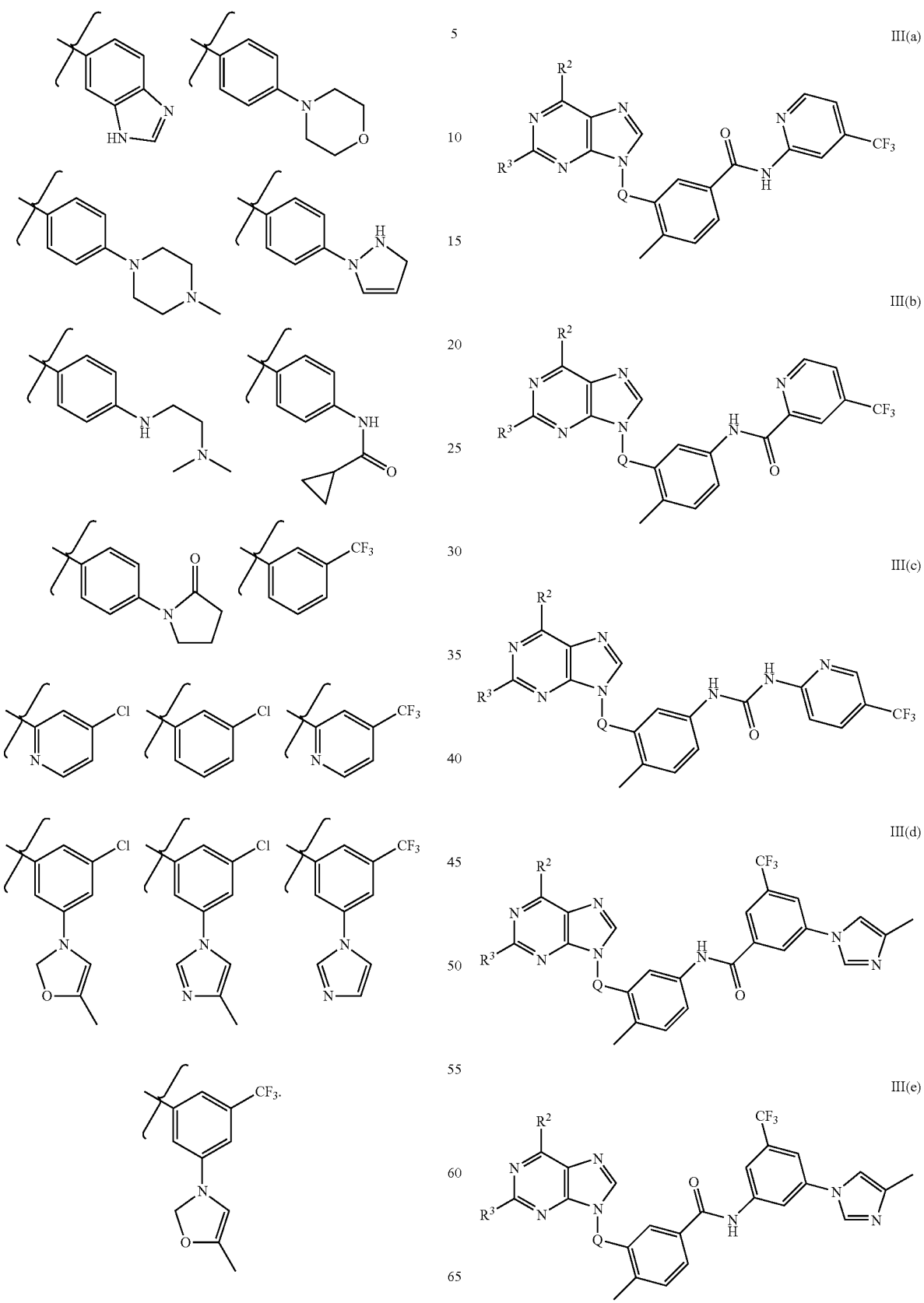

III(f)

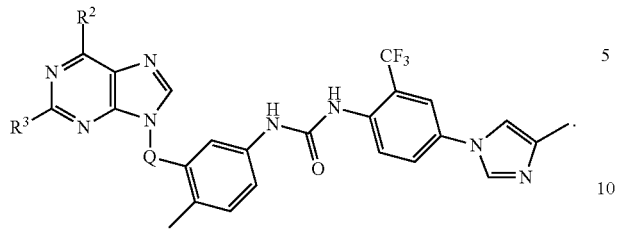

11. The compound of claim 5 in which $R^4$ is —CONR$^6$R$^7$ or —NHCONR$^6$R$^7$ where NR$^6$R$^7$ is a N-containing heterocyclic or heteroaryl ring system, C, as depicted below in Formula IV:

(IV)

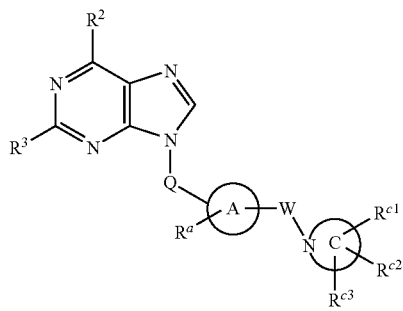

wherein ring C is bearing one or more optional substituents, $R^{c1}$, $R^{c2}$, $R^{c3}$ selected from the group consisting of halogen, —CN, —R, —OR, —SR, —S(O)$_n$R, —SO$_n$NRR', —NRR', —(CO)VR, —O(CO)VR, —NR(CO)VR, —S(CO)VR, or —VJ, —V—C(=NR)NR'R", —COCOR, —COM$_k$COR, —V—P(=O)(V'R)(V"R'), —NO$_2$, —NRSO$_2$R' and —NRSO$_2$NR'R" wherein V, V' and V" are independently —O—, —S—, —NR—, or a covalent bond; M is a substituted or unsubstituted methylene moiety; k is an integer from 0 to 4; n is 0, 1 or 2; m is an integer from 0 to 5; R is a hydrogen, an aliphatic, a heteroaliphatic, an aryl or heteroaryl; W is —CO— or —NHCO—.

12. The compound of claim 11 having one of the following structures:

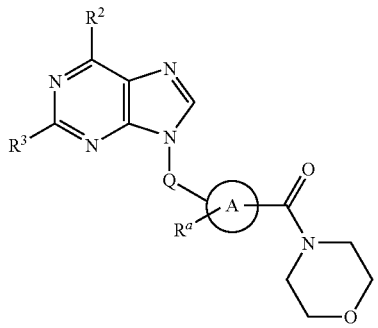

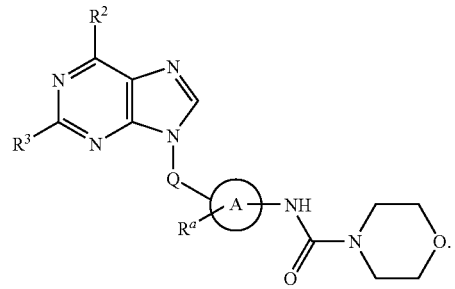

13. The compound of any of claims 1-12 in which $R^3$ is -M$_k$R$^C$, k is 0 and R$^C$ is —R, —OR or —NRR'.

14. The compound claim 1 in which $R^2$ is aliphatic or heteroaliphatic, including cyclic and acyclic such groups, which in either case may be substituted or unsubstituted.

15. The compound of claim 14 in which $R^2$ is a substituted or unsubstituted 3-7carbon cycloaliphatic group.

16. The compound of claim 1 in which $R^2$ is aryl or heteroaryl group which may be substituted or unsubstituted.

17. A composition comprising at least one compound of any of claims 1-12 or 14-16, or a salt thereof, and at least one pharmaceutically acceptable excipient or additive.

* * * * *